US006875831B1

(12) United States Patent
Kramer et al.

(10) Patent No.: US 6,875,831 B1
(45) Date of Patent: Apr. 5, 2005

(54) MONO AND MULTIFUNCTIONAL ALKOXYAMINES FOR THE PREPARATION OF FUNCTIONALIZED MACROMERS

(75) Inventors: Andreas Kramer, Meyriez (CH); Peter Nesvadba, Marly (CH); Marie-Odile Zink, Steinbach (FR); Wiebke Wunderlich, Bologna (IT)

(73) Assignee: CIBA Specialty Chemicals Corp., Tarrytown, NY (US)

(*) Notice: Subject to any disclaimer, the term of this patent is extended or adjusted under 35 U.S.C. 154(b) by 221 days.

(21) Appl. No.: 10/019,618
(22) PCT Filed: Jun. 26, 2000
(86) PCT No.: PCT/EP00/05899
§ 371 (c)(1), (2), (4) Date: Dec. 20, 2000
(87) PCT Pub. No.: WO01/02345
PCT Pub. Date: Jan. 11, 2001

(30) Foreign Application Priority Data

Jul. 2, 1999  (EP) ............................................. 99810567

(51) Int. Cl.$^7$ .......................... C08F 2/00; C07C 239/20
(52) U.S. Cl. ....................... 526/209; 526/204; 526/215; 544/63; 544/383; 546/192; 546/245; 560/37; 560/38; 564/300
(58) Field of Search ................. 564/300; 526/204, 526/209, 215, 220; 546/192, 245; 544/63, 383; 560/37, 38

(56) References Cited

U.S. PATENT DOCUMENTS

| 5,627,248 A | | 5/1997 | Koster et al. | |
| 5,677,388 A | | 10/1997 | Koster et al. | |
| 5,723,554 A | * | 3/1998 | Fujita et al. | 526/204 |
| 5,910,549 A | * | 6/1999 | Matyjaszewski et al. | 526/217 |

FOREIGN PATENT DOCUMENTS

| GB | 2342649 | 4/2000 |
| WO | 99/46261 | 9/1999 |

OTHER PUBLICATIONS

A. Kwang–Hyun et al., Synthetic Communications. vol. 28, No. 4, (1999), pp. 4361–4366.
S. Naoya et al., Polymer Preprints, vol. 40, No. 1, (1999), pp. 111–112.
I. Li et al., Polymer Preprints, vol. 40, No. 1, (1999), pp. 383–384.
M. Yozo et al., Macromolecules, vol. 31, No. 14, (1998), pp. 4659–4661.
I. Li et al., Polymer Preprints, vol. 39, No. 2, (1998), pp. 598–599.
D. Julian et al., Journal of Polymer Science: Part A: Polymer Chemistry, vol. 36, No. 12, (1998), pp. 2161–2167.

(Continued)

Primary Examiner—Fred Teskin
(74) Attorney, Agent, or Firm—Tyler A. Stevenson

(57) ABSTRACT

The invention pertains to a compound of formula (I), (II) or (III)

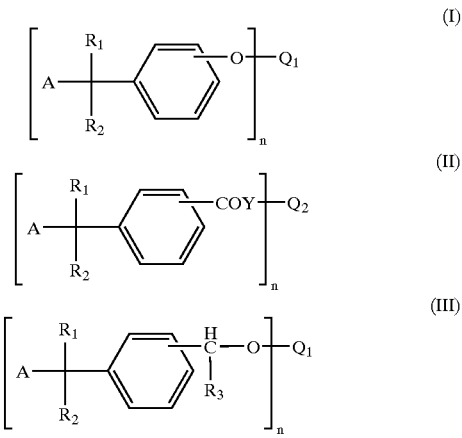

wherein $R_1$ and $R_2$ are independently of each other hydrogen, $C_1$–$C_{18}$alkyl, $C_3$–$C_{18}$alkenyl, $C_3$–$C_{18}$alkinyl or phenyl which are unsubstituted or substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; A is a group capable of forming a stable free nitroxyl radical A*, which is bound via its oxygen atom to the carbon atom; Y is O, $NR_3$ or $CHR_3$—$X_a$, wherein $X_a$ is O, S or $NR_3$; $R_3$ is hydrogen, $C_1$–$C_{18}$alkyl, $C_3$–$C_{18}$alkenyl, $C_3$–$C_{18}$alkinyl or phenyl which are unsubstituted or substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; $Q_1$ is an organic or inorganic radical, derived from a compound having at least one functional group being capable of reacting with a hydroxy group; $Q_2$ is an organic radical derived from a mono or polyfunctional alcohol, mono or polyfunctional aminoalcohol, mono or polyfunctional amine mono or polyfunctional mercaptane, mono or polyfunctional phenol or mono or polyfunctional thiophenol; and n is a number from 1 to 20; with the proviso, that in formula (I) if n is 1, $Q_1$ is not

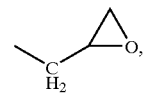

or if n is 2, $R_1$ is H and $R_2$ is —$CH_2$—O-tert-butyl, A is not 2,2,6,6-tetramethylpiperidine or 2,2,6,6-tetramethylpiperidine-4-carboxylic acid. Further subjects of the invention are a composition comprising above compounds and at least one ethylenically unsaturated monomer, process for polymerization and the (co)polymers obtained therefrom.

19 Claims, No Drawings

OTHER PUBLICATIONS

J. D. Druliner, Journal of Physical Organic Chemistry, vol. 8, No. 4, (1995), pp. 316–324.

K. Toyoji et al., Polymer Preprints, vol. 41, No. 1, (2000), pp. 938–939.

* cited by examiner

MONO AND MULTIFUNCTIONAL ALKOXYAMINES FOR THE PREPARATION OF FUNCTIONALIZED MACROMERS

The present invention relates to compounds having at least one, preferably multiple alkoxyamine functionality and to their precursors. Further objects of the invention are a composition comprising an ethylenically unsaturated monomer or oligomer and the alkoxyamine compound, a process for polymerization and the use of multifunctional alkoxyamines in radical polymerization processes.

The compounds of the present invention provide polymeric resin products having low polydispersity. The polymerization process proceeds with good monomer to polymer conversion efficiency. In particular, this invention relates to stable free radical-mediated polymerization processes which provide homopolymers, random copolymers, block copolymers, multiblock copolymers, graft copolymers and the like, at enhanced rates of polymerization and enhanced monomer to polymer conversions.

The multifunctional alkoxyamines of the present invention are particularly useful for the preparation of block copolymers, star (co)polymers, comb (co)polymers or other (co)polymers where a specific polymer architecture is desired.

Polymers or copolymers prepared by conventional free radical polymerization processes inherently have broad molecular weight distributions or polydispersities which are generally higher than about four. If a free radical polymerization process is to be used for producing narrow molecular weight distributions, then all polymer chains must be initiated at about the same time and termination of the growing polymer-chains by combination or disproportionation processes must be avoided.

Conventional radical polymerization reaction processes pose various significant problems, such as difficulties in predicting or controlling the molecular weight, the polydispersity and the modality of the polymers produced. Furthermore, free radical polymerization processes in bulk of the prior art are difficult to control because the polymerization reaction is strongly exothermic and an efficient heat removal in the highly viscous polymer is mostly impossible. The exothermic nature of the prior art free radical polymerization processes often severely restricts the concentration of reactants or the reactor size upon scale-up.

Due to the above mentioned uncontrollable polymerization reactions, gel formation in conventional free radical polymerization processes are also possible and cause broad molecular weight distributions and/or difficulties during filtering, drying and manipulating the product resin.

U.S. Pat. No. 4,581,429 to Solomon et al., issued Apr. 8, 1986, discloses a free radical polymerization process which controls the growth of polymer chains to produce short chain or oligomeric homopolymers and copolymers, including block and graft copolymers. The process employs an initiator having the formula (in part) R'R"N—O—X, where X is a free radical species capable of polymerizing unsaturated monomers. The reactions typically have low conversion rates. Specifically mentioned radical R'R"N—O* groups are derived from 1,1,3,3 tetraethylisoindoline, 1,1,3,3 tetrapropylisoindoline, 2,2,6,6 tetramethylpiperidine, 2,2,5,5 tetramethylpyrrolidine or di-t-butylamine. However, the suggested compounds do not fulfill all requirements. Particularly the polymerization of acrylates does not proceed fast enough and/or the monomer to polymer conversion is not as high as desired.

U.S. Pat. No. 5,627,248 and U.S. Pat. No. 5,677,388 disclose difunctional alkoxyamines which contain additionally a cleaving bond, through which they can act as radical initiators such as for example azo initiators, disulfide initiators, peroxide initiators and sulfur containing chain transfer agents.

However there is still a need for polymerization processes and for the preparation of narrow polydispersity polymeric resins with defined molecular weights using the economical free radical polymerization techniques. These polymerization processes will also control the physical properties of the polymers such as viscosity, hardness, gel content, processability, clarity, high gloss, durability, and the like.

The initiators/regulators, the polymerization processes and resin products of the present invention are useful in many applications, including a variety of specialty applications, such as for the preparation of block copolymers which are useful as compatibilizing agents for polymer blends, or dispersing agents for coating systems or for the preparation of narrow molecular weight resins or oligomers for use in coating technologies and thermoplastic films or as toner resins and liquid immersion development ink resins or ink additives used for electrophotographic imaging processes.

Surprisingly, it has now been found that the present compounds are very suitable to prepare (co)polymers particularly block, star, comb (co)polymers and the like.

By their multiple alkoxyamine functionality they provide an ideal tool for tailor made polymerization processes. The degree of branches can be chosen by selecting one, two, three, four or even more alkoxyamine functionalities.

Furthermore with the present invention there are provided initiators/regulators which allow very efficiently to bring into the macromer functional end-groups which come from the initiating radical. This is the case for monofunctional and multi-functional initiators/regulators. The compounds of the present invention thus allow to produce macromers or polymers with a wide variety of functional groups, which was not easily possible until now.

The functionalized macromers or polymers may then be further reacted with suitable modifying compounds to further adjust the polymer's properties.

Polymerization of the monomers results in a polymer or copolymer of narrow polydispersity and a high monomer to polymer conversion even at relatively low temperatures and at short reaction times, making the polymerization process particularly suitable for industrial applications. The resulting (co)polymers are of high purity and in many cases colorless, therefore not requiring any further purification.

One object of the present invention is a compound of formula (I) (II) or (III)

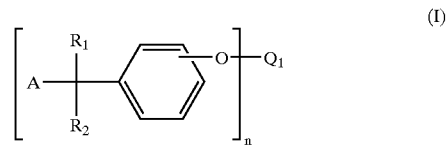

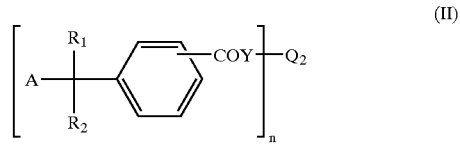

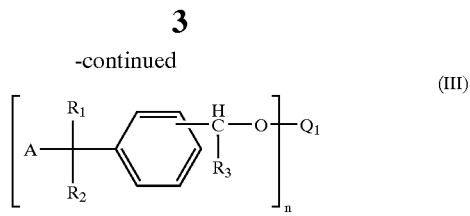

(III)

wherein

- $R_1$ and $R_2$ are independently of each other hydrogen, $C_1-C_{18}$alkyl, $C_3-C_{18}$alkenyl, $C_3-C_{18}$alkinyl or phenyl which are unsubstituted or substituted by $NO_2$, halogen, amino, hydroxy, cyano, carboxy, $C_1-C_4$alkoxy, $C_1-C_4$alkylthio, $C_1-C_4$alkylamino or di($C_1-C_4$alkyl)amino;
- A is a group capable of forming a stable free nitroxyl radical A*, which is bound via its oxygen atom to the carbon atom;
- Y is O, $NR_3$ or $CHR_3-X_a$, wherein $X_a$ is O, S or $NR_3$;
- $R_3$ is hydrogen, $C_1-C_{18}$alkyl, $C_3-C_{18}$alkenyl, $C_3-C_{18}$alkinyl or phenyl which are unsubstituted or substituted by $NO_2$, halogen, amino, hydroxy, cyano, carboxy, $C_1-C_4$alkoxy, $C_1-C_4$alkylthio, $C_1-C_4$alkylamino or di($C_1-C_4$alkyl)amino;
- $Q_1$ is an organic or inorganic radical, derived from a compound having at least one functional group being capable of reacting with a hydroxy group;
- $Q_2$ is an organic radical derived from a mono or polyfunctional alcohol, mono or polyfunctional aminoalcohol, mono or polyfunctional amine mono or polyfunctional mercaptane, mono or polyfunctional phenol or mono or polyfunctional thiophenol; and
- n is a number from 1 to 20;

with the proviso, that in formula (I) if n is 1, $Q_1$ is not

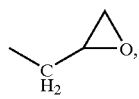

or if n is 2, $R_1$ is H and $R_2$ is —$CH_2$—O-tert-butyl, A is not 2,2,6,6-tetramethylpiperidine or 2,2,6,6-tetramethylpiperidine-4-carboxylic acid.

$Q_1$ in the meaning of an inorganic radical is for example derived from a halogenated inorganic acid derivative.

Preferably $Q_1$ is derived from an unsubstituted or substituted triazine, from a mono or multifunctional alkylating agent, from a mono or polycarboxylic acid or acid derivative, from a mono or polyepoxide, from a mono or polyisocyanate or from $POCl_3$, $SO_2Cl_2$, $BCl_3$ or $SiCl_4$.

Examples for $Q_1$ are given below.

a) Examples for mono or multifunctional triazines are: tri-, di-, or mono- chlorotriazine

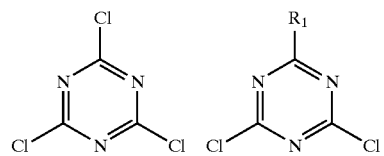

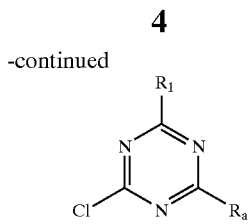

wherein $R_f$ and $R_e$ are $C_1-C_{18}$alkyl, phenyl, $C_1-C_{18}$alkoxy, $C_1-C_{18}$alkylthio, phenoxy, $NH(C_1-C_{18}$alkyl), $N(di-C_1-C_{18}$alkyl) or phenylthio. It is also possible to use the corresponding fluoro-triazines instead of chloro-triazines.

b) Alkylating agents are in principal known. Examples for mono- and multifunctional alkylating agents are:

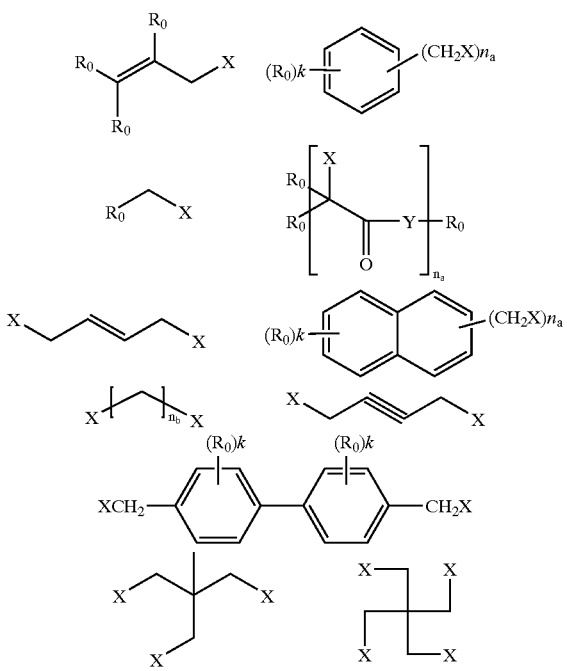

wherein X is a leaving group such as for example halogen, an aliphatic or aromatic sulfonate such as toluene sulfonate or methane sulfonate;

$Y_1$ is O, NH or $N(C_1-C_{18})$alkyl; and k and $n_a$ are numbers from 1 to 10, $n_b$ is a number from 1 to 20; and $R_0$ may be hydrogen or any aromatic or aliphathic substituent, such as for example unsubstituted or substituted $C_1-C_{18}$alkyl or phenyl.

Also suitable is allylchloride as alkylating agent, leading to an allyl group as $Q_1$.

c) Examples for mono, di- and polycarboxylic acids, acid chlorides, anhydrides or esters are:

Aliphatic mono carboxylic acids or their derivatives, which can contain 2 to 20 carbon atoms. Typical examples are acetic acid, acetyl chloride, acetic acid anhydride, propionic acid and derivatives, stearylic acid, laurylic acid and the corresponding derivatives.

The aliphatic dicarboxylic acids can contain 2 to 40 carbon atoms, the cycloaliphatic dicarboxylic acids 6 to 10 carbon atoms, the aromatic dicarboxylic acids 8 to 14 carbon atoms, the aliphatic hydroxycarboxylic acids 2 to 12 carbon atoms and the aromatic and cycloaliphatic hydroxycarboxylic acids 7 to 14 carbon atoms.

Suitable dicarboxylic acids are linear and branched saturated aliphatic dicarboxylic acids, aromatic dicarboxylic acids and cycloaliphatic dicarboxylic acids. Suitable aliphatic dicarboxylic acids are those containing 2 to 40 carbon atoms, for example oxalic acid, malonic acid, dimethylmalonic acid, succinic acid, pimelic acid, adipic acid, trimethyladipic acid, sebacic acid, azelaic acid and dimeric acids (dimerisation products of unsaturated aliphatic carboxylic acids such as oleic acid), alkylated malonic and succinic acids, such as octadecylsuccinic acid.

Suitable cycloaliphatic dicarboxylic acids are: 1,3-cyclobutanedicarboxylic acid, 1,3-cyclopentanedicarboxylic acid, 1,3- and 1,4-cyclohexanedicarboxylic acid, 1,3- and 1,4-(dicarboxylmethyl)cyclohexane, 4,4'-dicyclohexyldicarboxylic acid.

Suitable aromatic dicarboxylic acids are: in particular terephthalic acid, isophthalic acid, o-phthalic acid, and 1,3-, 1,4-, 2,6- or 2,7-naphthalenedicarboxylic acid, 4,4'-diphenyldicarboxylic acid, 4,4'-diphenylsulfonedicarboxylic acid, 4,4'-benzophenonedicarboxylic acid, 1,1,3-trimethyl-5-carboxyl-3-(p-carboxylphenyl)indane, 4,4'-diphenyletherdicarboxylic acid, bis-p-(carboxylphenyl) methane or bis-p-(carboxylphenyl)ethane. Examples for more than difunctional acids are trimellitic acid, citric acid, pyromellitic acid or itaconic acid.

The above carboxylic acids and acid derivatives are also examples for the substituent R in formula (XXXA) defined hereinafter.

d) Examples of reactive derivatives of inorganic acids are $POCl_3$, $SO_2Cl_2$, $SiCl_4$ which leads for example to compounds such as

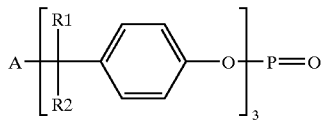

e) The epoxy compounds which can be used in the context of the invention may have an aliphatic, aromatic, cycloaliphatic, araliphatic or heterocyclic structure; they include epoxy groups as side groups. The epoxy groups are preferably attached to the rest of the molecule as glycidyl groups by way of ether or ester linkages, or else the compounds are N-glycidyl derivatives of heterocyclic amines, amides or imides. Epoxy compounds of these types are widely known and are obtainable commercially.

They lead for example to compounds such as

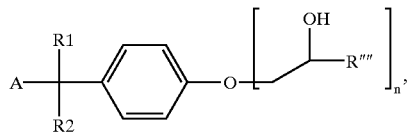

wherein R"" denotes an organic radical derived from the corresponding epoxy compound and n is as defined above. The epoxy compounds comprise epoxy radicals, especially those of the formula

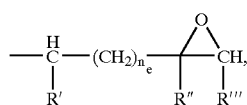

which are attached directly to carbon, oxygen, nitrogen or sulfur atoms and in which R' and R''' are both hydrogen, R" is hydrogen or methyl and $n_e$ is 0, or in which R' and R''' together are —$CH_2$—$CH_2$— or —$CH_2$—$CH_2$—$CH_2$—, R" in that case is hydrogen, and $n_e$ is 0 or 1.

Examples of epoxy compounds that may be mentioned are:

I) Polyglycidyl esters and poly(β-methylglycidyl) esters obtainable by reacting a compound having at least two carboxyl groups in the molecule with epichlorohydrin and/or glyceroldichlorohydrin and/or β-methylepichlorohydrin. The reaction is judiciously carried out in the presence of bases. Compounds having at least two carboxyl groups in the molecule that can be used are aliphatic polycarboxylic acids. Examples of these polycarboxylic acids are glutaric, adipic, pimelic, suberic, azelaic, sebacic or dimerized or trimerized linoleic acid.

Alternatively, cycloaliphatic polycarboxylic acids can be employed, examples being tetrahydrophthalic, 4-methyltetrahydrophthalic, hexahydrophthalic or 4-methylhexahydrophthalic acid.

It is also possible to use aromatic polycarboxylic acids, such as phthalic, isophthalic, trimellitic and pyromellitic acid.

Likewise employable are carboxyl-terminated adducts of, for example, trimellitic acid and polyols such as glycerol or 2,2-bis(4-hydroxycyclohexyl)propane.

II) Polyglycidyl ethers or poly(β-methylglycidyl) ethers obtainable by reacting a compound having at least two free alcoholic hydroxyl groups and/or phenolic hydroxyl groups with a suitably substituted epichlorohydrin under alkaline conditions or in the presence of an acidic catalyst with subsequent alkali treatment.

Ethers of this type are derived, for example, from acyclic alcohols, such as ethyleneglycol, diethyleneglycol and higher poly(oxyethylene) glycols, propane-1,2-diol, or poly (oxy-propylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, bis-trimethylolpropane, pentaerythritol, sorbitol, and from polyepichlorohydrins.

They are alternatively derived, for example, from cycloaliphatic alcohols, such as 1,3- or 1,4-dihydroxycyclohexane, bis(4-hydroxycyclohexyl)methane, 2,2-bis(4-hydroxycyclohexyl)propane or 1,1-bis (hydroxymethyl)cyclohex-3-ene, or they possess aromatic nuclei, such as N,N-bis(2-hydroxyethyl)aniline or p,p'-bis (2-hydroxyethylamino)diphenylmethane.

The epoxy compounds may also be derived from mononuclear phenols, such as resorcinol or hydroquinone; or else they are based on polynuclear phenols, such as on bis(4-hydroxyphenyl)methane, 2,2-bis(4-hydroxyphenyl)propane, 2,2-bis(3,5-dibromo-4-hydroxyphenyl)propane or 4,4'-dihydroxydiphenyl sulfone, or on condensates of phenols with formaldehyde that are obtained under acidic conditions, such as phenol novolaks.

III) Poly(N-glycidyl) compounds obtainable by dehydrochlorinating the reaction products of epichlorohydrin with amines containing at least two amino hydrogen atoms. These amines are, for example, aniline, toluidine, n-butylamine, bis(4-aminophenyl)methane, m-xylylene-diamine or bis(4-methylaminophenyl)methane, and also N,N,O-triglycidyl-m-aminophenol or N,N,O-triglycidyl-p-aminophenol.

The poly(N-glycidyl) compounds also include N,N'-diglycidyl derivatives of cycloalkyleneureas, such as ethyleneurea or 1,3-propyleneurea, and N,N'-diglycidyl derivatives of hydantoins, such as of 5,5-dimethylhydantoin.

IV) Poly(S-glycidyl) compounds, such as di-S-glycidyl derivatives derived from dithiols, such as ethane-1,2-dithiol or bis(4-mercaptomethylphenyl) ether.

V) Epoxy compounds in which R' and R''' together are —$CH_2$—$CH_2$— and $n_e$ is 0 are bis(2,3-epoxycyclopentyl)

ether, 2,3-epoxycyclopentyl glycidyl ether or 1,2-bis(2,3-epoxycyclopentyloxy)ethane. An example of an epoxy resin having a radical of the formula in which R' and R''' together are —$CH_2$—$CH_2$— and $n_e$ is 1 is (3,4-epoxy-6-methylcyclohexyl)methyl 3',4'-epoxy-6'-methylcyclohexanecarboxylate.

f) Mono and polyfunctional isocyanates are well known and a wide variety is commercially available. The isocyanates lead to the following structure

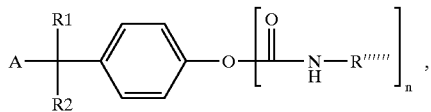

wherein R'''' denotes an aliphatic or aromatic organic radical derived from the isocyanate compound and n is as defined above.

Examples of isocyanates are di-, tri- or tetra isocyanates. Diisocyanates are widely used in the industry and most of them are commercially available. Preferred diisocyanates are those in which the bridge group between the isocyanate groups is formed by a linear or branched aliphatic $C_2$–$C_{20}$alkyl which is unsubstituted or mono- or polysubstituted by $C_1$–$C_6$ alkyl or $C_1$–$C_6$alkoxy, $C_3$–$C_8$cycloalkyl or heterocycloalkyl which is unsubstituted or mono- or polysubstituted by $C_1$–$C_6$alkyl or $C_1$–$C_6$alkoxy, linear or branched aliphatic $C_2$–$C_{20}$alkyl which is interrupted by unsubstituted or $C_1$–$C_6$alkyl- or $C_1$–$C_6$alkoxy-substituted $C_3$–$C_8$cycloalkyl or heterocycloalkyl and is unsubstituted or substituted by $C_1$–$C_6$alkyl or $C_1$–$C_6$alkoxy, phenyl, naphthyl, biphenyl or $C_3$–$C_{10}$heteroaryl which is unsubstituted or mono- or polysubstituted by $C_1$–$C_6$alkyl or $C_1$–$C_6$alkoxy, or linear or branched aliphatic $C_2$–$C_{20}$alkyl which is interrupted by phenyl, naphthyl or $C_3$–$C_{10}$heteroaryl and is unsubstituted or substituted by $C_1$–$C_6$alkyl or $C_1$–$C_6$alkoxy.

The linear or branched $C_1$–$C_{20}$alkyl radicals are, for example, methyl, ethyl and the various position isomers of propyl, butyl, pentyl, hexyl, heptyl, octyl, nonyl, decyl, undecyl, dodecyl, tridecyl, tetradecyl, pentadecyl or hexadecyl, heptadecyl, octadecyl, nonadecyl or eicosyl.

The $C_1$–$C_6$alkoxy radicals can be linear or branched and are, for example, methoxy, ethoxy and the various positional isomers of propoxy, butoxy, pentoxy or hexoxy.

Heterocycloalkyl is, for example, pyrrolidine, piperidine, morpholine, oxazolidine, dioxolane, or an isocyanuric acid triester group.

$C_3$–$C_8$cycloalkyl is, for example, cyclopropyl, dimethylcyclopropyl, cyclobutyl, cyclopentyl, methylcyclopentyl, cyclohexyl, cycloheptyl or cyclooctyl.

Aromatic means, for example, phenyl, naphthyl or anthracenyl.

Heteroaromatic means, for example, pyridine, pyrimidine, pyrrole, furan, imidazole, pyrazole or triazine.

Specific examples of diisocyanates are 1,6-bis[isocyanato]hexane, 5-isocyanato-3-(isocyanatomethyl)-1,1,3-trimethylcyclohexane, 1,3-bis[5-isocyanato-1,3,3-trimethyl-phenyl]-2,4-dioxo-1,3-diazetidine, 3,6-bis[9-isocyanatononyl]-4,5-di(1-heptenyl)cyclohexene, bis[4-isocyanatocyclohexyl]methane, trans-1,4-bis[isocyanato]cyclohexane, 1,3-bis[isocyanatomethyl]benzene, 1,3-bis[1-isocyanato-1-methylethyl]benzene, 1,4-bis[2-isocyanatoethyl]cyclohexane, 1,3-bis[isocyanatomethyl]cyclohexane, 1,4-bis[1-isocyanato-1-methylethyl]benzene, bis[isocyanato]isododecylbenzene, 1,4-bis[isocyanato]benzene, 2,4-bis[isocyanato]toluene, 2,6-bis[isocyanato]toluene, 2,4-/2,6-bis[isocyanato]toluene, 2-ethyl-1,2,3-tris[3-isocyanato-4-methylanilinocarbonyloxy]propane, N,N'-bis[3-isocyanato-4methylphenyl]urea, 1,4-bis[3-isocyanato-4-methylphenyl]-2,4-dioxo-1,3-diazetidine, 1,3,5-tris[3-isocyanato-4-methylphenyl]-2,4,6-trioxohexahydro-1,3,5-triazine, 1,3-bis[3-isocyanato-4-methylphenyl]-2,4,5-trioxoimidazolidine, bis[2-isocyanatophenyl]methane, (2-isocyanatophenyl)(4-isocyanato-phenyl)methane, bis[4-isocyanatophenyl]methane, 2,4-bis[4-isocyanatobenzyl]-1-isocyanatobenzene, [4-isocyanato-3-(4-isocyanatobenzyl)phenyl][2-isocyanato-5-(4-isocyanatobenzyl)phenyl]methane, tris[4-isocyanatophenyl]methane, 1,5-bis[isocyanato]naphthalene, or 4,4'-bis[isocyanato]-3,3'-dimethylbiphenyl.

$Q_2$ is an organic radical derived from a mono or polyfunctional alcohol, mono or polyfunctional aminoalcohol, mono or polyfunctional amine, mono or polyfunctional mercaptane, mono or polyfunctional phenol or mono or polyfunctional thiophenol.

The aliphatic mono or polyfunctional alcohol can contain 2 to 12 carbon atoms, the cycloaliphatic polyols 5 to 8 carbon atoms and the aromatic polyols 6 to 16 carbon atoms.

Polyoxyalkylene glycols having a molecular weight from 150 to 40000 can also be used.

Aromatic polyols are those, wherein at least two hydroxyl groups are bound to one or to different aromatic hydrocarboxylic radicals.

Suitable aliphatic polyols are for example diols which are linear or branched aliphatic glycols, in particular those containing 2 to 12, preferably 2 to 6, carbon atoms in the molecule, for example: ethylene glycol, 1,2- and 1,3-propylene glycol, 1,2-, 1,3-, 2,3- or 1,4-butanediol, pentyl glycol, neopentyl glycol, 1,6-hexanediol, 1,12-dodecanediol. A suitable cycloaliphatic diol is, for example, 1,4-dihydroxycyclohexane. Other suitable aliphatic diols are, for example, 1,4-bis(hydroxymethyl)cyclohexane, aromatic-aliphatic diols, such as p-xylylene glycol or 2,5-dichloro-p-xylylene glycol, 2,2-(β-hydroxyethoxyphenyl)propane and polyoxyalkylene glycols, such as diethylene glycol, triethylene glycol, polyethylene glycol or polypropylene glycol. The alkylenediols are preferably linear and preferably contain 2 to 4 carbon atoms.

Other suitable aliphatic diols are the β-hydroxyalkylated, in particular β-hydroxyethylated bisphenols, such as 2,2-bis[4'-(β-hydroxyethoxy)phenyl]propane.

Another group of suitable aliphatic diols are the heterocyclic diols described in the German published patent specifications 1812003, 2342432, 2342372 and 2453326. Examples are: N,N'-bis(β-hydroxethyl)-5,5-dimethylhydantoin, N,N'-bis(β-hydroxypropyl)-5,5-dimethylhydantoin, methylenebis-[N-(β-hydroxyethyl)-5-methyl-5-ethylhydantoin], methylenebis-[N-(β-hydroxyethyl)-5,5-dimethylhydantoin], N,N'-bis(β-hydroxyethyl)benzimidazolone, N,N'-bis(β-hydroxyethyl)-(tetrachloro)benzimidazolone or N,N'-bis(β-hydroxyethyl)-(tetrabromo)benzimidazolone.

Suitable aromatic diols are mononuclear diphenols and, in particular, dinuclear diphenols carrying a hydroxyl group at each aromatic nucleus. The term aromatic will be taken to mean preferably hydrocarbonaromatic radicals such as phenylene or naphthylene. Besides e.g. hydroquinone, resorcinol or 1,5-, 2,6- and 2,7-dihydroxynaphthalene, bisphenols merit particular mention.

A suitable triol is for example

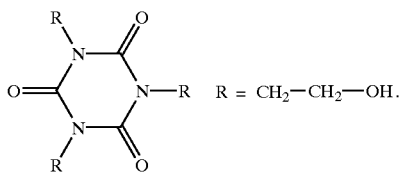

Examples of bisphenols are: bis(p-hydroxyphenyl) ether or bis(p-hydroxyphenyl) thioether, bis(p-hydroxyphenyl) sulfone, bis(p-hydroxyphenyl)methane, bis(4-hydroxyphenyl)-2,2'-biphenyl, phenylhydroquinone, 1,2-bis(p-hydroxyphenyl)ethane, 1-phenyl-bis(p-hydroxyphenyl)methane, diphenyl-bis(p-hydroxyphenyl)methane, diphenyl-bis(p-hydroxyphenyl)ethane, bis(3,5-dimethyl-4-hydroxyphenyl)sulfone, bis(3,5-dimethyl-4-hydroxyphenyl)-p-diisopropylbenzene, bis(3,5-dimethyl-4-hydroxyphenyl)-m-diisopropylbenzene, 2,2-bis(3',5'-dimethyl-4'-hydroxyphenyl)propane, 1,1- or 2,2-bis(p-hydroxyphenyl)butane, 2,2-bis(p-hydroxyphenyl)hexafluoropropane, 1,1-dichloro- or 1,1,1-trichloro-2,2-bis(p-hydroxyphenyl)ethane, 1,1-bis(p-hydroxyphenyl)cyclopentane and, in particular, 2,2-bis(p-hydroxyphenyl)propane (bisphenol-A) and 1,1-bis(p-hydroxyphenyl)cyclohexane (bisphenol-C).

The polyaminoalcohols or polyamines can be deduced from the above mentioned polyalcohols by replacing one or more hydroxylgroups by amino groups.

Primary amine groups are preferred, which may be attached to aromatic rings or alkyl groups as mentioned above for the corresponding alcohols.

Examples of further polyalcohols are erythrose, threose or are derived from hexoses or pentoses, such as glucose, fructose, mannose, galactose, talose allose altrose, xylose, lyxose, ribose or arabinose or their corresponding reduced forms.

Suitable mercaptanes or thiophenols are those which are derived by substituting the oxygen atom by a sulfur atom in the above mentioned examples.

Preferred is a compound of formula (I), (II) or (III) wherein $R_1$ and $R_2$ are independently of each other hydrogen, $C_1$–$C_{12}$alkyl, $C_3$–$C_{12}$alkenyl or phenyl.

More preferably $R_1$ and $R_2$ are independently of each other hydrogen or $C_1$–$C_4$alkyl, most preferably hydrogen or methyl.

Preferred is a compound of formula (II), wherein Y is O or $NR_3$.

More preferred is a compound of formula (II) wherein Y is O.

Also preferred is a compound of formula (I), (II) or (III) wherein n is a number from 2–10, more preferably from 2–6 and most preferably from 2–4.

Preferably $Q_1$ is an organic radical derived from an unsubstituted or substituted triazine, from a mono or polycarboxylic acid or acid derivative, from a mono or multifunctional alkylating agent or from a mono or polyisocyanate.

More preferably $Q_1$ is an organic radical derived from an unsubstituted or substituted triazine, from a polycarboxylic acid or polycarboxylic acid derivative, having 2–6 carboxylgroups, from a multifunctional alkylating agent having 2–6 functional groups or from a polyisocyanate, having 2–6 isocyanate groups.

Examples for $Q_1$ have already been mentioned.

Preferably $Q_2$ is an organic radical derived from a polyfunctional alcohol, a polyfunctional aminoalcohol or a polyfunctional amine.

More preferably $Q_2$ is a radical derived from a polyalcohol having 2–6 hydroxy groups, a polyaminoalcohol having 2–6 amino and/or hydroxy groups, or a polyamine having 2–6 amine groups.

Examples for $Q_2$ have already been mentioned.

The radicals $Q_1$ and $Q_2$ do not contain a labile bond which may cleave at a temperature below the temperature, necessary to cleave the N—O—C bond to which the radical A is attached, liberating the stable nitroxyl radical N—O* and the initiating C-centered radical. In particular groups such as —O—O—, —N=N— or —O—C(O)—O— are not part of the groups $Q_1$ or $Q_2$.

The radical A* derived from the group A can be a stable open chain nitroxyl radical or a cyclic nitroxyl radical.

Preferred is a stable cyclic nitroxyl radical.

In formula (I), (II) or (III) A is preferably a group of formula (X)

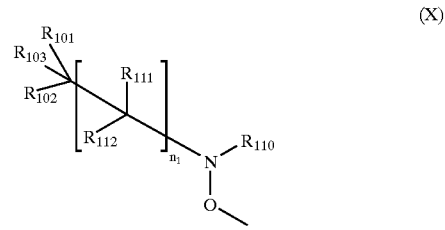

wherein $n_1$ is 0 or 1

$R_{101}$, $R_{102}$, $R_{103}$ are each independently of one another hydrogen, halogen, $NO_2$, cyano, —$CONR_{105}R_{106}$, —($R_{109}$)$COOR_{104}$, —C(O)—$R_{107}$, —$OR_{108}$, —$SR_{108}$, —$NHR_{108}$, —$N(R_{108})_2$, carbamoyl, di($C_1$–$C_{18}$alkyl)carbamoyl, —C(=$NR_{105}$)($NHR_{106}$);

unsubstituted $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, which is unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino;

or $R_{102}$ and $R_{103}$, together with the linking carbon atom, form a $C_3$–$C_{12}$cycloalkyl radical, a ($C_4$–$C_{12}$cycloalkanon)-yl radical or a $C_3$–$C_{12}$cycloalkyl radical containing at least one O atom and/or a $NR_{108}$ group; or if $n_1$ is 1

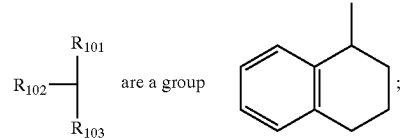

$R_{104}$ is hydrogen, $C_1$–$C_{18}$alkyl, phenyl, an alkali metal cation or a tetraalkylammonium cation;

$R_{105}$ and $R_{106}$ are hydrogen, $C_1$–$C_{18}$alkyl, $C_2$–$C_{18}$alkyl which is substituted by at least one hydroxy group or, taken together, form a $C_2$–$C_{12}$alkylene bridge or a $C_2$–$C_{12}$-alkylene bridge interrupted by at least one O or/and $NR_{108}$ atom;

$R_{107}$ is hydrogen, $C_1$–$C_{18}$alkyl or phenyl;

$R_{108}$ is hydrogen, $C_1$–$C_{18}$alkyl or $C_2$–$C_{18}$alkyl which is substituted by at least one hydroxy group;

$R_{109}$ is $C_1$–$C_{12}$alkylen or a direct bond;

$R_{110}$ is $C_4$–$C_{18}$alkyl bound via a tertiary C-atom to the nitrogen atom, $C_9$–$C_{11}$phenylalkyl, $C_3$–$C_{12}$cycloalkyl or $C_3$–$C_{12}$cycloalkyl containing at least one nitrogen or oxygen atom; or $C_4$–$C_{18}$alkyl bound via a tertiary C-atom to the nitrogen atom, $C_9$–$C_{11}$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino;

if $n_1$ is 1

$R_{111}$ is $C_1$–$C_{18}$alkyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino; or a polycyclic cycloaliphatic ring system or a polycyclic cycloaliphatic ring system with at least one di- or trivalent nitrogen atom; or $R_{110}$ and $R_{111}$ together form a $C_2$–$C_{12}$alkylene bridge, a $C_3$–$C_{12}$alkylen-on bridge or a $C_2$–$C_{12}$alkylene bridge which is interrupted by at least one O or N atom, which bridges are unsubstituted or substituted with $C_1$–$C_{18}$alkyl, hydroxy($C_1$–$C_4$)alkyl, phenyl, $C_7$–$C_9$phenylalkyl, $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino, $R_{112}$ is hydrogen, —($R_{109}$)$COOR_{104}$, cyano, —$OR_{108}$, —$SR_{108}$, —$NHR_{108}$, —$N(R_{108})_2$, —NH—C(O)—$R_{108}$, unsubstituted $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_2$–$C_{18}$alkenyl, $C_2$–$C_{18}$ alkynyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino, di($C_1$–$C_4$alkyl)amino; or $R_{111}$ and $R_{112}$ together with the linking carbon atom form a $C_3$–$C_{12}$cycloalkyl radical;

or A is a group of formula XXa, XXb or XXc

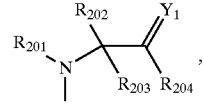
(XXa)

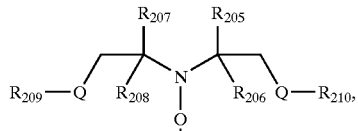
(XXb)

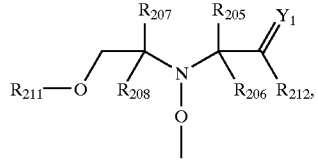
(XXc)

wherein $Y_1$ is O or $CH_2$;

Q is O or $NR_{220}$, wherein $R_{220}$ is hydrogen or $C_1$–$C_{18}$alkyl;

$R_{201}$ is tertiary $C_4$–$C_{18}$alkyl or phenyl, which are unsubstituted or substituted by halogen, OH, $COOR_{221}$ or C(O)—$R_{222}$ wherein $R_{221}$ is hydrogen, a alkali metal atom or $C_1$–$C_{18}$alkyl and $R_{222}$ is $C_1$–$C_{18}$alkyl; or $R_{201}$ is $C_5$–$C_{12}$cycloalkyl, $C_5$–$C_{12}$cycloalkyl which is interrupted by at least one O or N atom, a polycyclic alkyl radical or a polycyclic alkyl radical which is interrupted by at least one O or N atom;

$R_{202}$ and $R_{203}$ are independently $C_1$–$C_{18}$alkyl, benzyl, $C_5$–$C_{12}$cycloalkyl or phenyl, which are unsubstituted or substituted by halogen, OH, $COOR_{221}$ or C(O)—$R_{222}$ or together with the carbon atom form a $C_5$–$C_{12}$cycloalkyl ring;

if $Y_1$ is O, $R_{204}$ and $R_{212}$ are OH, O(alkali-metal) $C_1$–$C_{18}$alkoxy, benzyloxy, $NR_{223}R_{224}$, wherein $R_{223}$ and $R_{224}$ are independently from each other hydrogen, $C_1$–$C_{18}$alkyl or phenyl, which are unsubstituted or substituted by halogen, OH, $COOR_{221}$ or C(O)—$R_{222}$;

if $Y_1$ is $CH_2$, $R_{204}$ is OH, $C_1$–$C_{18}$alkoxy, benzyloxy, O—C(O)—($C_1$–$C_{18}$)alkyl or $NR_{223}R_{224}$;

$R_{212}$ are a group C(O)$R_{225}$, wherein $R_{225}$ is OH, $C_1$–$C_{18}$alkoxy, benzyloxy, $NR_{223}R_{224}$, wherein $R_{223}$ and $R_{224}$ are independently from each other hydrogen, $C_1$–$C_{18}$alkyl or phenyl, which are unsubstituted or substituted by halogen, OH, $COOR_{221}$ or C(O)—$R_{222}$;

$R_{205}$, $R_{206}$, $R_{207}$ and $R_{208}$ are independently of each other $C_1$–$C_{18}$alkyl, $C_5$–$C_{12}$cycloalykyl or phenyl; or $R_{205}$ and $R_{206}$ and/or $R_{207}$ and $R_{208}$ together with the carbon atom form a $C_5$–$C_{12}$cycloalkyl ring;

$R_{209}$ and $R_{210}$ are independently of each other hydrogen, formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, $COOR_{221}$ or

C(O)—$R_{222}$;

$R_{211}$, is formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, $COOR_{221}$ or C(O)—$R_{222}$;

or A is a group containing a structural element of formula (XXX)

$$\text{(XXX)}$$

wherein $G_1$, $G_2$, $G_3$, $G_4$ are independently $C_1$–$C_6$alkyl or $G_1$ and $G_2$ or $G_3$ and $G_4$, or $G_1$ and $G_2$ and $G_3$ and $G_4$ together form a $C_5$–$C_{12}$cycloalkyl group;

$G_5$, $G_6$ independently are H, $C_1$–$C_{18}$alkyl, phenyl, naphthyl or a group $COOC_1$–$C_{18}$alkyl or A is a group of formula (XLa) or (XLb)

$$\text{(XLa)}$$

$$\text{(XLb)}$$

wherein $R_{301}$, $R_{302}$, $R_{303}$ and $R_{304}$ independently of each other are $C_1$–$C_{18}$alkyl, $C_3$–$C_{18}$alkenyl, $C_3$–$C_{18}$alkinyl, or $C_1$–$C_{18}$alkyl, $C_3$–$C_{18}$alkenyl, $C_3$–$C_{18}$alkinyl which are substituted by OH, halogen or a group —O—C(O)—$R_{305}$, $C_2$–$C_{18}$alkyl which is interrupted by at least one O atom and/or $NR_{305}$ group, $C_3$–$C_{12}$cycloalkyl or $C_6$–$C_{10}$aryl or $R_{301}$ and $R_{302}$ and/or $R_{303}$ and $R_{304}$ together with the linking carbon atom form a $C_3$–$C_{12}$cycloalkyl radical;

$R_{305}$, $R_{306}$ and $R_{307}$ independently are hydrogen, $C_1$–$C_{18}$alkyl or $C_6$–$C_{10}$aryl;

$Z_1$ is O or $NR_{308}$;

$R_{308}$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by one or more OH, halogen or a group —O—C(O)—$R_{305}$, $C_2$–$C_{18}$alkyl which is interrupted by at least one O atom and/or $NR_{305}$ group, $C_3$–$C_{12}$cycloalkyl or $C_6$–$C_{10}$aryl, $C_7$–$C_9$phenylalkyl, $C_5$–$C_{10}$heteroaryl, —C(O)—$C_1$–$C_{18}$alkyl, —O—$C_1$–$C_{18}$alkyl or —$COOC_1$–$C_{18}$alkyl;

$Q_4$ is a direct bond or a divalent radical $CR_{309}R_{310}$, $CR_{309}R_{310}$—$CR_{311}R_{312}$, $CR_{309}R_{310}CR_{311}R_{312}CR_{313}R_{314}$, C(O) or $CR_{309}R_{310}C(O)$, wherein $R_{309}$, $R_{310}$, $R_{311}$, $R_{312}$, $R_{313}$ and $R_{314}$ are independently hydrogen, phenyl or $C_1$–$C_{18}$alkyl.

Halogen is Fluorine, Chlorine, Bromine or Iodine, preferably Chlorine or Bromine.

The alkyl radicals in the various substituents may be linear or branched. Examples of alkyl containing 1 to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

$C_5$–$C_{12}$cycloalkyl is typically, cyclopentyl, methylcyclopentyl, dimethylcyclopentyl, cyclohexyl, methylcyclohexyl.

Cycloalkyl which is interrupted by at least one O or N atom is for example 2-tetrahydropyran-yl, tetrahydrofurane-yl, 1,4 dioxan-yl, pyrrolidin-yl, tetrahydrothiophen-yl, pyrazolidin-yl, imidazolidin-yl, butyrolactone-yl, caprolactame-yl.

Examples for alkali metal are lithium, sodium or potassium.

Alkyl substituted by-OH is typically 2-hydroxyethyl, 2-hydroxypropyl or 2-hydroxybutyl.

$C_1$–$C_{18}$ alkoxy is for example methoxy, ethoxy, propoxy, butoxy, pentoxy, octoxy, dodecyloxy or octadecyloxy.

$C_1$–$C_{18}$Alkyl substituted by $C_1$–$C_8$alkoxy, preferably by $C_1$–$C_4$alkoxy, in particular by methoxy or ethoxy, is typically 2-methoxyethyl, 2-ethoxyethyl, 3-methoxypropyl, 3-ethoxypropyl, 3-butoxypropyl, 3-octoxypropyl and 4-methoxybutyl.

$C_1$–$C_{18}$Alkyl substituted by di($C_1$–$C_4$alkyl)amino is preferably e.g. dimethylamino, diethylamino, 2-dimethylaminoethyl, 2-diethylaminoethyl, 3-dimethylaminopropyl, 3-diethylaminopropyl, 3-dibutylaminopropyl and 4-diethylaminobutyl.

$C_1$–$C_{18}$Alkyl substituted by $C_1$–$C_4$alkylamino is preferably e.g. methylamino, ethylamino, 2-methylaminoethyl, 2-ethylaminoethyl, 3-methylaminopropyl, 3-ethylaminopropyl, 3-butylaminopropyl and 4-ethylaminobutyl.

$C_1$–$C_4$Alkylthio is typically methylthio, ethylthio, propylthio, isopropylthio, butylthio and isobutylthio.

$C_2$–$C_{18}$alkylcarbonyl is for example acetyl, propionyl, butyryl, pentylcarbonyl, hexylcarbonyl or dodecylcarbonyl.

$C_7$–$C_9$phenylalkyl is for example benzyl, phenylethyl or phenylpropyl.

$C_3$–$C_{18}$alkyl interrupted by at least one O atoms is for example —$CH_2$—$CH_2$—O—$CH_2$—$CH_3$, —$CH_2$—$CH_2$—O—$CH_3$ or —$CH_2$—$CH_2$—O—$CH_2$—$CH_2$—$CH_2$—O—$CH_2$—$CH_3$. It is preferably derived from polyethylene glycol. A general description is —$((CH_2)_a$—$O)_b$—$H/CH_3$, wherein a is a number from 1 to 6 and b is a number from 2 to 10.

Examples of $C_2$–$C_{12}$alkylene bridges, preferably of $C_2$–$C_6$alkylene bridges, are ethylene, propylene, butylene, pentylene, hexylene.

$C_2$–$C_{12}$alkylene bridges interrupted by at least one N or O atom are, for example, —$CH_2$—O—$CH_2$—$CH_2$—, —$CH_2$—O—$CH_2$—$CH_2$—$CH_2$—, —$CH_2$—O—$CH_2$—$CH_2$—$CH_2$—$CH_2$—, —$CH_2$—O—$CH_2$—$CH_2$—O—$CH2$—, —$CH_2$—NH—$CH_2$—$CH_2$—, —$CH_2$—NH—$CH_2$—$CH_2$—$CH_2$—, —$CH_2$—NH—$CH_2$—$CH_2$—$CH_2$—$CH_2$—, —$CH_2$—NH—$CH_2$—$CH_2$—NH—$CH2$— or —$CH_2$—NH—$CH_2$—$CH_2$—O—$CH2$—.

Examples for $C_4$–$C_{12}$cycloalkanone-yl are cyclopentanone-yl, cyclohexanone-yl or cycloheptanone-yl.

Phenyl substituted by 1, 2 or 3 $C_1$–$C_4$alkyl or $C_1$–$C_4$alkoxy is typically methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of polycyclic cycloaliphatic ring systems are adamantane, cubane, twistane, norbornane, bycyclo[2.2.2]octane or bycyclo[3.2.1]octane.

An example of a polycyclic heterocycloaliphatic ring system is hexamethylenetetramine (urotropine).

Examples of monocarboxylic acids with 1 to 18 carbon atoms are formic acid, acetic acid, propionic acid, phenyl acetic acid, cyclohexane carbonic acid, mono-, di- and trichlor-acetic acid or mono-, di- and trifluor-acetic acid. Other suitable acids are benzoic acid, chlor-benzoic acid, methanesulfonic acid, ethanesulfonic acid, benzenesulfonic acid, p-toluenesulfonic acid, chlorbenzenesulfonic acid, trifluormethanesulfonic acid, methylphosphonic acid or phenylphosphonic acid.

$C_2$–$C_{12}$alkanoyl is, for example, propionyl, butyryl, octanoyl, dodecanoyl, but preferably acetyl.

$C_4$–$C_{12}$alkenylene is, in particular, 2-butenylene, 2-pentenylene or 3-hexenylene.

$C_6$–$C_{12}$arylene is, for example, o-, m- or p-phenylene, 1,4-naphthylene or 4,4'-diphenylene.

The carboxylic acid radicals mentioned above are in each case taken to mean radicals of the formula (—CO)$_x$R, where x is as defined above, and the meaning of R arises from the definition given.

$C_1$–$C_{18}$alkanoyloxy is, for example, formyloxy, acetyloxy, propionyloxy, butyryloxy, valeryloxy, lauroyloxy, palmitoyloxy and stearoyloxy.

A monovalent radical of a carboxylic acid is for example, an acetyl, caproyl, stearoyl, acryloyl, methacryloyl, benzoyl or β-(3,5-di-tert-butyl-4-hydroxyphenyl)propionyl radical. A monovalent silyl radical is for example, a radical of the formula —($C_jH_{2j}$)—Si(Z')$_2$Z", in which j is an integer in the range from 2 to 5, and Z' and Z", independently of one another, are $C_1$–$C_4$alkyl or $C_1$–$C_4$alkoxy.

A divalent radical of a dicarboxylic acid, it is, for example, a malonyl, succinyl, glutaryl, adipoyl, suberoyl, sebacoyl, maleoyl, itaconyl, phthaloyl, dibutylmalonyl, dibenzylmalonyl, butyl(3,5-di-tert-butyl-4-hydroxybenzyl)malonyl or bicycloheptenedicarbonyl radical.

Further suitable acids have already been mentioned in the explanation of $Q_1$.

The nitroxyl radicals which are the precursors of the group A of formula (X) are known and ma be prepared according to WO 99/03984, EP-A-0 891 986 or WO 98/13392.

Some typical examples are given below.

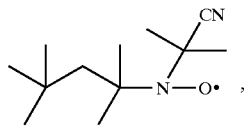

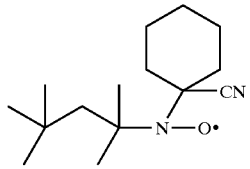

-continued

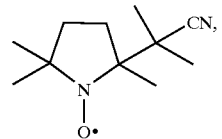

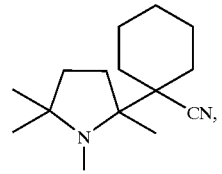

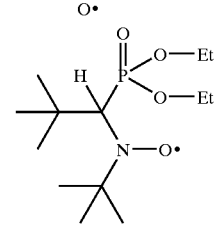

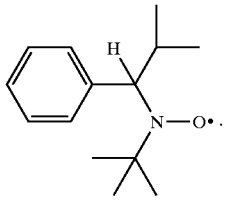

The nitroxyl radicals which are precursors of the group A of formula XXa, b and c are also known and may be prepared according to WO 00/07981

Typical examples are given below.

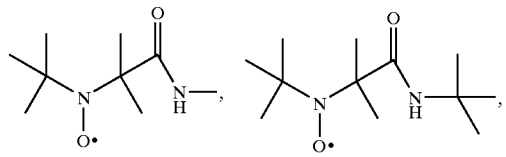

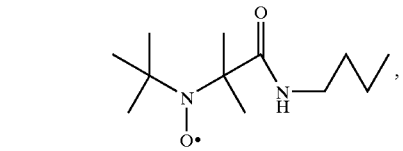

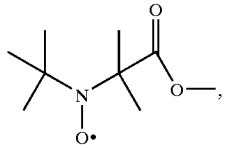

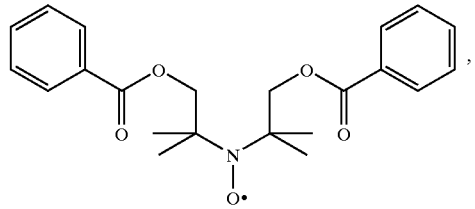

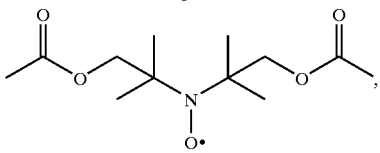

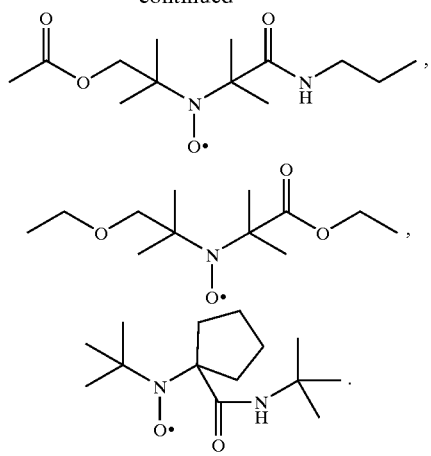

The nitroxyl radicals which are precursors of the group A of formula XXX are also known and can be prepared as described in GB 2335190.

Furthermore DE 26 21 841, U.S. Pat. No. 4,131,599 and DE 26 30 798 for examples describe the preparation of 2,6-diethyl-2,3,6-trimethyl-4-oxopiperidine and 2,6-dipropyl-3-ethyl-2,6-dimethyl-4-oxopiperidine, which are intermediates for the corresponding 1-oxo compounds.

Another method for the preparation of 2,2-dimethyl-6,6-dialkyl-4-oxopiperidine is described by F. Asinger, M. Thiel, H. Baltz, Monatshefte für Chemie 88, 464 (1957) or by J. Bobbittt et al. in J. Org. Chem. 58, 4837 (1993).

The oxidation of the piperidine compound to 1-oxo-piperidine derivatives is well known in the art and for example described by L. B. Volodarsky, V. A. Reznikov, V. I. Ovcharenko in Synthetic Chemistry of Stable Nitroxides, CRC Press, Boca Raton 1994.

The 2,2,6,6-tetramethylpiperidine precursors are known and partially commercially available.

Examples are given below.

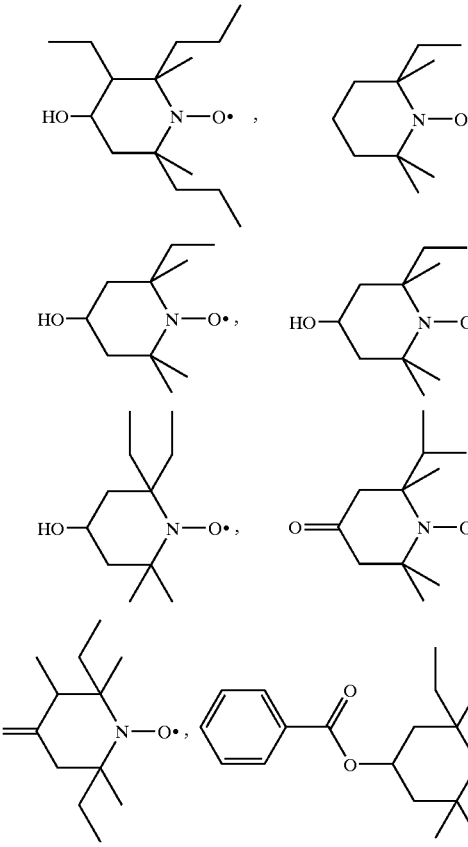

The nitroxyl radicals which are precursors of the group A of formula XL are also known.

The compounds can be prepared according to WO 98/30601, WO 98/44008 or GB 2342649.

Some typical examples are given below.

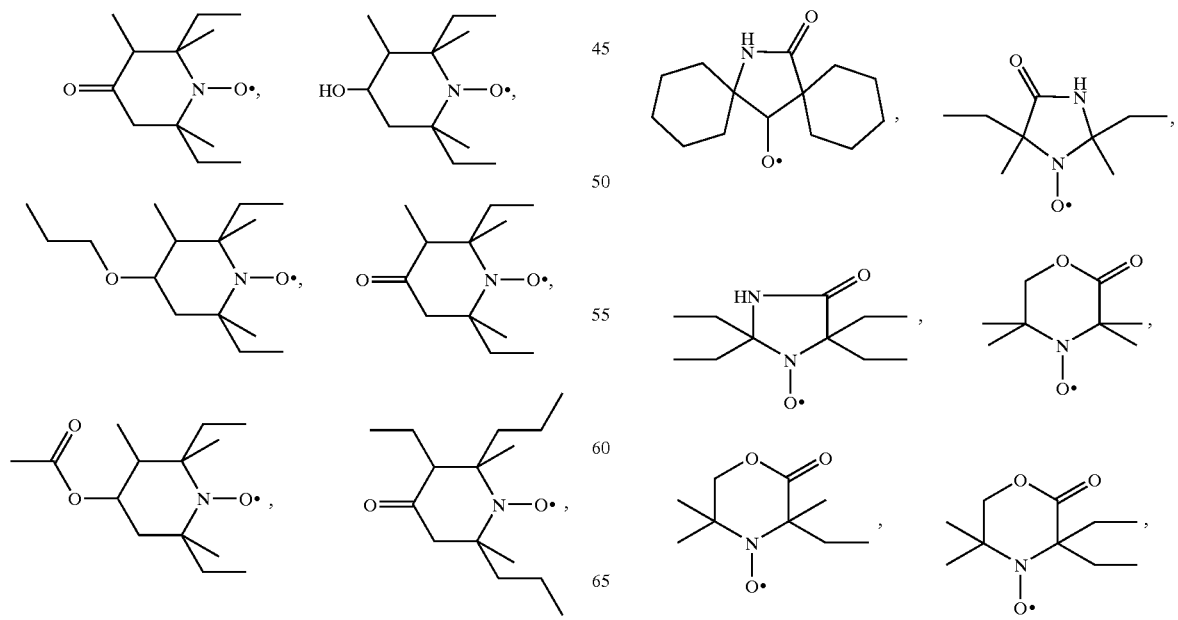

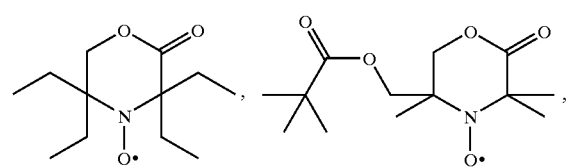
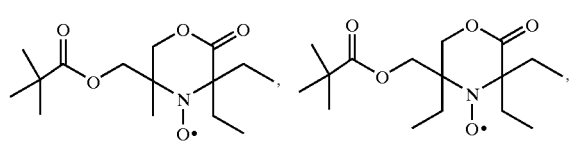
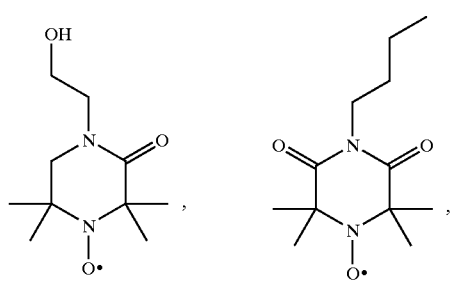
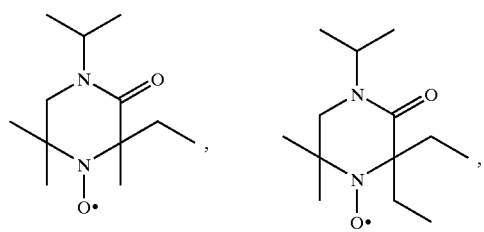
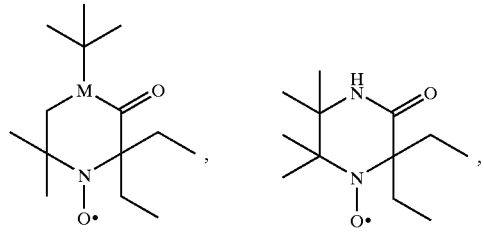
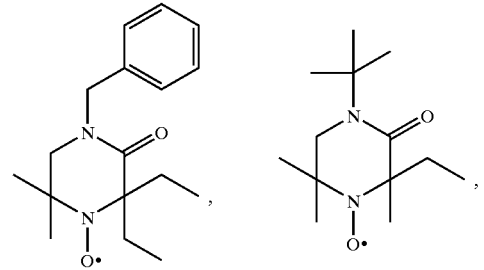
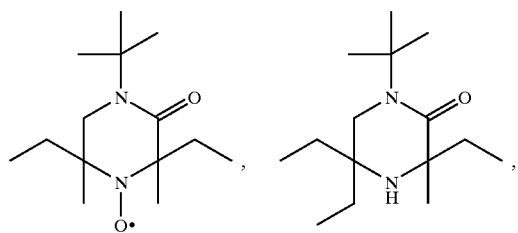
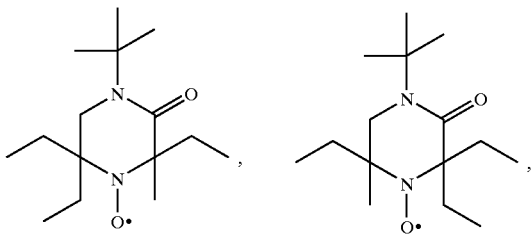
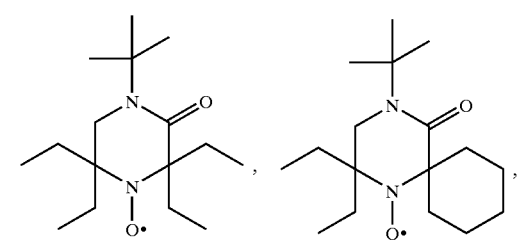
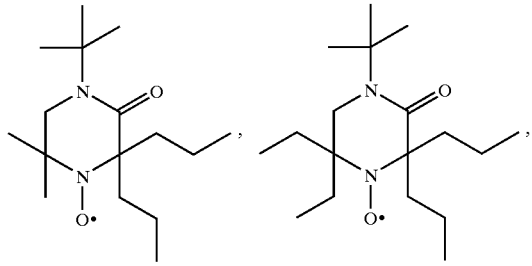
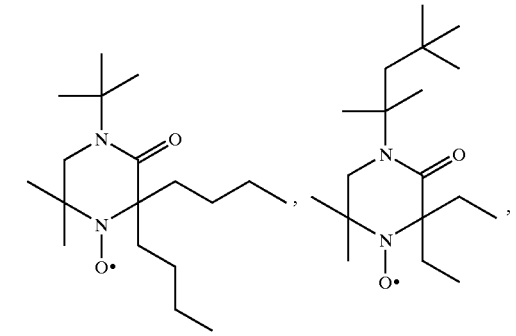
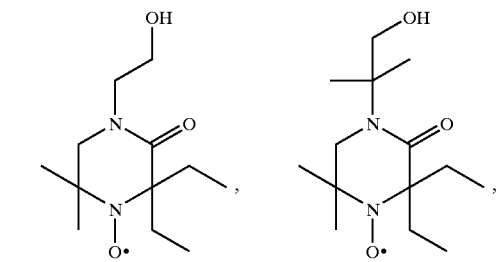
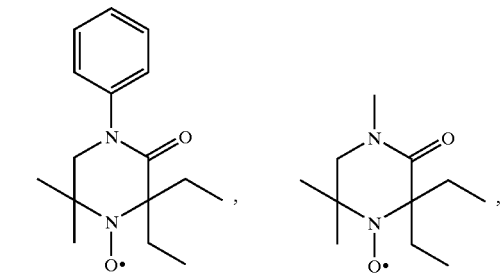

-continued

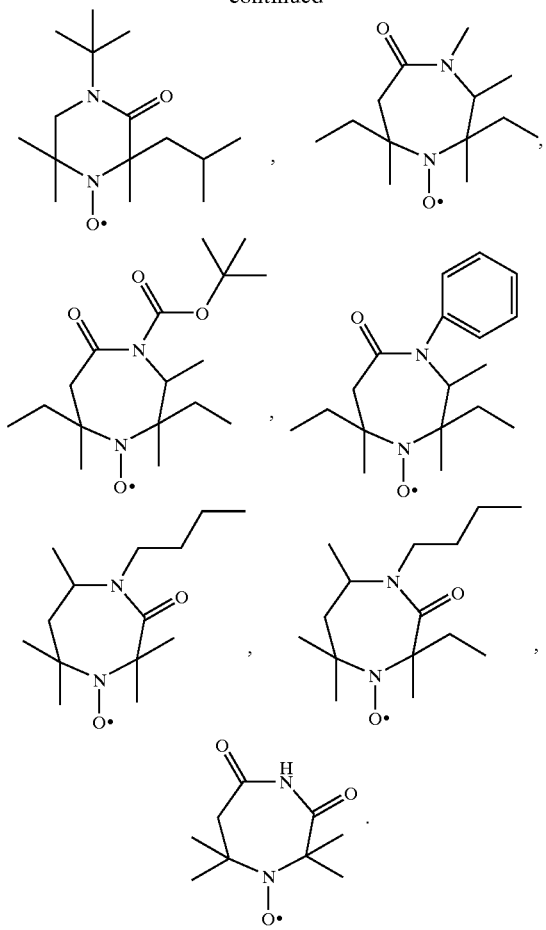

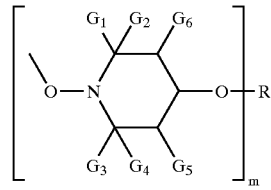

benzyl or phenyl and $R_{212}$ is OH, $C_1$–$C_{18}$alkoxy, benzyloxy, $NR_{223}R_{224}$, wherein $R_{223}$ and $R_{224}$ are independently of each other hydrogen or $C_1$–$C_{18}$alkyl;

or wherein A is a group of formula (XXXA), (XXXB) or (XXXO)

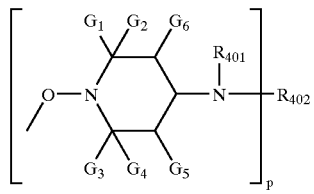

(XXXA)

(XXXB)

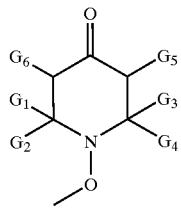

(XXXO)

Preferred compounds are those of formula (I) or (II), wherein A is a group of formula (X) $n_1$ is 1 $R_{101}$ is cyano; $R_{102}$ and $R_{103}$ are each independently of one another unsubstituted $C_1$–$C_{12}$alkyl or phenyl; or $R_{102}$ and $R_{103}$, together with the linking carbon atom, form a $C_5$–$C_7$ cycloalkyl radical;

$R_{110}$ is $C_4$–$C_{12}$alkyl bound via a tertiary C-atom to the nitrogen atom, $C_9$–$C_{11}$phenylalkyl or phenyl; $R_{11}$ is $C_1$–$C_{18}$alkyl, $C_7$–$C_9$phenylalkyl or $C_3$–$C_{12}$cycloalkyl; or $R_{110}$ and $R_{111}$ together form a $C_2$–$C_6$alkylene bridge which is unsubstituted or substituted with $C_1$–$C_4$alkyl; and $R_{112}$ is $C_1$–$C_4$alkyl;

or wherein A is a group of formula (XXa) $R_{201}$ is tertiary $C_4$–$C_8$alkyl; $R_{202}$ and $R_{203}$ are methyl, ethyl or together with the carbon atom form a $C_5C_6$cycloalkyl ring;

$R_{204}$ is $C_1$–$C_{18}$alkoxy, benzyloxy or $NR_{223}R_{224}$, wherein $R_{223}$ and $R_{224}$ are independently of each other hydrogen or $C_1$–$C_8$alkyl;

or wherein A is a group of formula (XXb), wherein Q is O; $R_{205}$, $R_{206}$, $R_{207}$ and $R_{208}$ are independently of each other methyl or ethyl; or $R_{205}$ and $R_{206}$ and/or $R_{207}$ and $R_{208}$ together with the carbon atom form a $C_5$–$C_6$cycloalkyl ring; $R_{209}$ and $R_{10}$ are independently of each other formyl, $C_2$–$C_8$alkylcarbonyl, benzoyl, $C_7$–$C_8$alkyl, benzyl or phenyl;

or wherein A is a group of formula (XXc), wherein $Y_1$ is O; $R_{205}$, $R_{206}$, $R_{207}$ and $R_{208}$ are independently of each other methyl or ethyl; or $R_{205}$ and $R_{206}$ and/or $R_{207}$ and $R_{208}$ together with the carbon atom form a $C_5$–$C_6$cycloalkyl ring; $R_{211}$ is formyl, $C_2$–$C_{18}$alkylcarbonyl, benzoyl, $C_1$–$C_{18}$alkyl, wherein $G_1$, $G_2$, $G_3$ and $G_4$ are independently alkyl of 1 to 4 carbon atoms, or $G_1$ and $G_2$ together and $G_3$ and $G_4$ together, or $G_1$ and $G_2$ together or $G_3$ and $G_4$ together are pentamethylene; $G_5$ and $G_6$ are independently hydrogen or $C_1$–$C_4$ alkyl; m is a number from 1–4; p is a number from 1–3; R, if m is 1, is hydrogen, $C_1$–$C_{18}$alkyl which is uninterrupted or $C_2$–$C_{18}$alkyl which is interrupted by one or more oxygen atoms, cyanoethyl, benzoyl, glycidyl, a monovalent radical of an aliphatic carboxylic acid having 2 to 18 carbon atoms, of a cycloaliphatic carboxylic acid having 7 to 15 carbon atoms, or an α,β-unsubstituted carboxylic acid having 3 to 5 carbon atoms or of an aromatic carboxylic acid having 7 to 15 carbon atoms, where each carboxylic acid can be substituted in the aliphatic, cycloaliphatic, cycloaliphatic or aromatic moiety by 1 to 3-$COOZ_{12}$ groups, in which $Z_{12}$ is H, $C_1$–$C_{20}$ alkyl, $C_3$–$C_{12}$alkenyl, $C_5$–$C_7$cycloalkyl, phenyl or benzyl; or R is a monovalent radical of a carbamic acid or phosphorus-containing acid or a monovalent silyl radical; R, if m is 2, is $C_2$–$C_{12}$alkylene, $C_4$–$C_{12}$alkenylene, xylylene, a divalent radical of an aliphatic dicarboxylic acid having 2 to 36 carbon atoms, or a cycloaliphatic or aromatic dicarboxylic acid having 8–14 carbon atoms or of an aliphatic, cycloaliphatic or aromatic dicarbamic acid having 8–14 carbon atoms, where each dicarboxylic acid may be substituted in the aliphatic, cycloaliphatic or aromatic moiety by one or two —$COOZ_{12}$ groups; or R is a divalent radical of a phosphorus-containing acid or a divalent silyl radical; R, if m is 3, is a trivalent radical of an aliphatic, cycloaliphatic or aromatic tricarboxylic acid, which may be substituted in the aliphatic, cycloaliphatic or aromatic moiety by —COOZ$_{12}$, of an aromatic tricarbamic acid or of a phosphorus-containing acid, or is a trivalent silyl radical, R, if m is 4, is a tetravalent radical of an aliphatic, cycloaliphatic or aromatic tetracarboxylic acid; p is 1, 2 or 3, R$_{401}$ is C$_1$–C$_{12}$alkyl, C$_5$–C$_7$cycloalkyl, C$_7$–C$_8$aralkyl, C$_2$–C$_{16}$alkanoyl, C$_3$–C$_5$alkenoyl or benzoyl; when p is 1, R$_{402}$ is C$_1$–C$_{18}$alkyl, C$_5$–C$_7$cycloalkyl, C$_2$–C$_8$alkenyl unsubstituted or substituted by a cyano, carbonyl or carbamide group, or is a glycidyl, a group of the formula —CH$_2$CH(OH)—Z$_4$ or of the formula —CO—Z$_4$— or —CONH—Z$_4$ wherein Z$_4$ is hydrogen, methyl or phenyl; or when p is 2, R$_{402}$ is C$_2$–C$_{12}$alkylene, C$_6$–C$_{12}$arylene, xylylene, a —CH$_2$CH(OH)CH$_2$—O—B—O—CH$_2$CH(OH)CH$_2$— group, wherein B is C$_2$–C$_{10}$alkylene, C$_6$—C$_{15}$alkylene, C$_6$—C$_{15}$arylene or C$_6$–C$_{12}$cycloalkylene; or, provided that R$_{401}$ is not alkanoyl, alkenoyl or benzoyl; or R$_{402}$ is a divalent acyl radical of an aliphatic, cycloaliphatic or aromatic dicarboxylic acid or dicarbamic acid, or is the group —CO—; or R$_{401}$ and R$_{402}$ together when p is 1 can be the cyclic acyl radical of an aliphatic or aromatic 1,2- or 1,3-dicarboxylic acid; or R$_{402}$ is a group

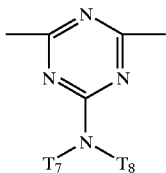

where T$_7$ and T$_8$ are independently hydrogen, alkyl of 1 to 18 carbon atoms, or T$_7$ and T$_8$ together are alkylene of 4 to 6 carbon atoms or 3-oxapentamethylene; when p is 3, R$_{402}$ is 2,4,6-triazinyl;

or wherein in formula (XLa) or (XLb) R$_{301}$, R$_{302}$, R$_{303}$ and R$_{304}$ independently of each other are C$_1$–C$_4$alkyl, which is unsubstituted or substituted by OH, or a group —O—C(O)—R$_{305}$, or R$_{301}$ and R$_{302}$ and/or R$_{303}$ and R$_{304}$ together with the linking carbon atom form a C$_5$–C$_6$cycloalkyl, radical; R$_{305}$ is hydrogen of C$_1$–C$_4$alkyl. R$_{306}$ and R$_{307}$ independently are hydrogen, methyl or ethyl; Z$_1$ is O or NR$_{308}$. Q$_4$ is a direct bond or a divalent radical CH$_2$, CH$_2$CH$_2$, CH$_2$—CH$_2$—CH$_2$, C(O), CH$_2$C(O) or CH$_2$— CH—CH$_3$, R$_{308}$ is hydrogen, C$_1$–C$_4$alkyl, C$_{1-C4}$alkyl which is substituted by OH, or benzyl.

More preferred is a compound, wherein in formula (XXXA), (XXXB) or (XXXO) G$_1$ and G$_3$ are methyl and G$_2$ and G$_4$ are ethyl or propyl, or G$_1$ and G$_2$ are methyl and G$_3$ and G$_4$ are ethyl or propyl.

Particularly preferred is a compound of formula (XXXA) wherein G$_1$ and G$_3$ are methyl and G$_2$ and G$_4$ are ethyl or propyl, or G$_1$ and G$_2$ are methyl and G$_3$ and G$_4$ are ethyl or propyl, one of G$_5$ and G$_6$ is hydrogen and the other is methyl or both are hydrogen, m is 1 and R is C$_1$–C$_{18}$alkyl or the monovalent radical of a C$_2$–C$_{18}$carboxylic acid.

Preferably in formula (XLa) and (XLb) at least two of R$_{301}$, R$_{302}$, R$_{303}$ and R$_{304}$ are ethyl, propyl or butyl and the remaining are methyl and the other substituents have the meaning as defined above.

The compounds of the present invention can be prepared according to standard methods as illustrated in examples A1–A18, which are however not comprehensive.

Particularly suitable intermediates are of formula (IV), (V), (VI) or (VII)

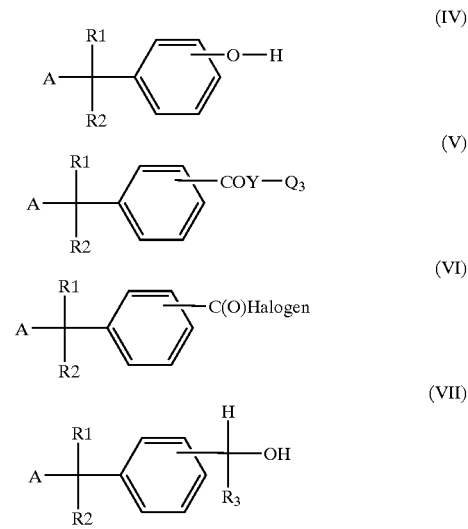

wherein R$_1$, R$_2$, R$_3$ and A are as defined above; Y is O, NR$_3$ or CR$_3$–R$_4$; Q$_3$ is hydrogen or C$_1$–C$_4$alkyl; and R$_4$ is hydrogen or halogen; with the proviso, that if in formula (V) Y is CR$_3$R$_4$ and R$_3$, R$_4$ and Q$_3$ are hydrogen A is not a nitroxyl radical derived from 2,2,6,6-tatramethyl-piperidine.

Compounds according to formula (IV), (V), (VI) or (VII) are also subject of the present invention. They can be prepared by reacting a stable free nitroxyl radical with the corresponding substituted aromatic compound. This can be done for example in a photoreaction as described in examples 1, 2, 11, 12, 16 and 23, compounds 101, 102, 111, 112, 116 and 123.

The intermediate compounds (IV), (V), (VI) and (VII) can further be reacted according to known methods to yield compounds of formula (I), (II) or (III). These reactions are standard operations such as for example alkylation, esterification, urethane formation or addition to oxirane groups.

A further subject of the present invention is a polymerizable composition, comprising a) at least one ethylenically unsaturated monomer or oligomer, and b) a compound of formula (I), (II), (III), (IV), (V), (VI) or (VII).

Preferably b) is a compound of formula (I) or (II).

The definitions are preferences given above apply also for the composition.

Typically the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl) acrylic acidanhydrides, (alkyl)acrylic acid salts, (alkyl) acrylic esters, (meth)acrylonitriles, (alkyl)acrylamides, vinyl halides or vinylidene halides.

Preferably ethylenically unsaturated monomers are ethylene, propylene, n-butylene, i-butylene, isoprene, 1,3-butadiene, α-C$_5$–C$_{18}$alkene, styrene, α-methyl styrene, p-methyl styrene or a compound of formula CH$_2$=C(R$_a$)—(C=Z)—R$_b$, wherein R$_a$ is hydrogen or C$_1$–C$_4$alkyl, R$_b$ is NH$_2$, O$^-$(Me$^+$), glycidyl, unsubstituted C$_1$–C$_{18}$alkoxy, C$_2$–C$_{100}$alkoxy interrupted by at least one N and/or O atom, or hydroxy-substituted C$_1$–C$_{18}$alkoxy, unsubstituted C$_1$–C$_{18}$alkylamino, di(C$_1$–C$_{18}$alkyl)amino, hydroxy-substituted C$_1$–C$_{18}$alkylamino or hydroxy-substituted di($C_1$–$C_{18}$alkyl)amino, —O—$CH_2CH_2$—N($CH_3$)$_2$ or —O—$CH_2$—$CH_2N^+H(CH_3)_2$ An$^-$; An$^-$ is a anion of a monovalent organic or inorganic acid; Me is a monovalent metal atom or the ammonium ion. Z is oxygen or sulfur.

Examples for $R_a$ as $C_2$–$C_{100}$alkoxy interrupted by at least one O atom are of formula

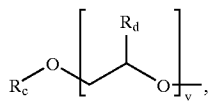

wherein $R_c$ is $C_1$–$C_{25}$alkyl, phenyl or phenyl substituted by $C_1$–$C_{18}$alkyl, $R_d$ is hydrogen or methyl and v is a number from 1 to 50. These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

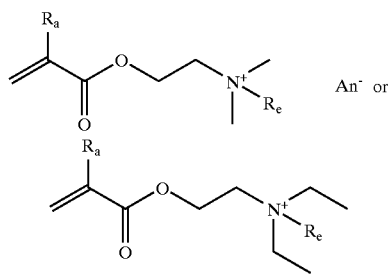

An$^-$, wherein An$^-$ and $R_a$ have the meaning as defined above and $R_e$ is methyl or benzyl. An$^-$ is preferably Cl$^-$, Br$^-$ or $^-O_3S$—$CH_3$.

Further acrylate monomers are

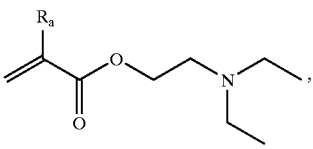

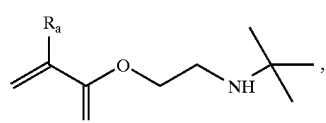

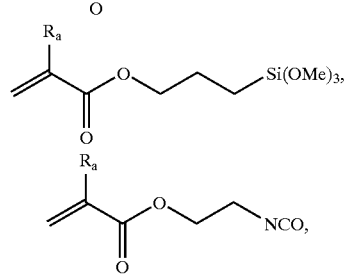

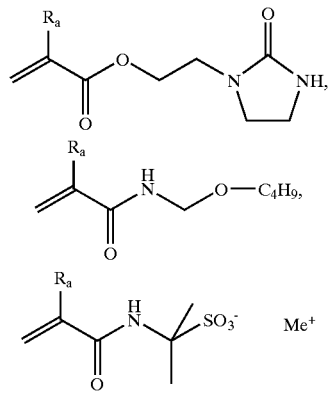

Examples for suitable monomers other than acrylates are

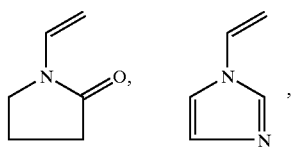

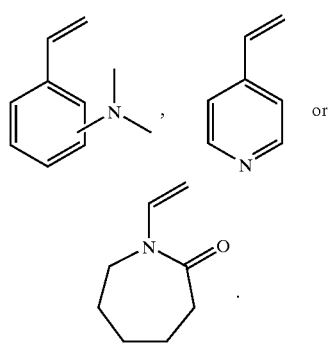

Preferably $R_a$ is hydrogen or methyl, $R_b$ is $NH_2$, gycidyl, unsubstituted or with hydroxy substituted $C_1$–$C_4$alkoxy, unsubstituted $C_1$–$C_4$alkylamino, di($C_1$–$C_4$alkyl)amino, hydroxy-substituted $C_1$–$C_4$alkylamino or hydroxy-substituted di($C_1$–$C_4$alkyl)amino; and Z is oxygen.

Particularly preferred ethylenically unsaturated monomers are styrene, methylacrylate, ethylacrylate, butylacrylate, isobutylacrylate, tert, butylacrylate, hydroxyethylacrylate, hydroxypropylacrylate, dimethylaminoethylacrylate, glycidylacrylates, methyl (meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth) acrylates, acrylonitrile, acrylamide, methacrylamide or dimetylaminopropyl-methacrylamide.

It is also possible to enhance the rate of polymerization or copolymerization of slowly polymerizing monomers such as for example of the class of methacrylates, in particular methylmethacrylate by the addition of more readily polymerizable comonomers such as acrylates. Typical examples are the polymerization or copolymerization of methylmethacrylate in the presence of methacrylate or butylacrylate.

Typical slowly polymerizing methacrylates are methyl (meth) acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth) acrylates, methacrylamide or dimethylaminopropyl-methacrylamide. The polymerization of these methacrylates can be enhanced by the addition of the corresponding acrylates.

Preferred is a composition wherein the ethylenically unsaturated monomer is a mixture of a methacrylate and an acrylate.

The amounts of readily polymerizable comonomers range typically from 5 parts to 95 and the slowly polymerizable monomers range from 95 to 5 parts respectively.

The initiator/regulator compound of formula (I), (II), (III), (IV), (V, (VI) or (VII) is preferably present in an amount of from 0.01 mol-% to 30 mol-%, more preferably in an amount of from 0.01 mol-% to 20 mol-%, and most preferably in an amount of from 0.05 mol-% to 10 mol-% based on the monomer or monomer mixture.

A further subject of the invention is a process for preparing an oligomer, a cooligomer, a polymer or a copolymer (block or random) by free radical polymerization of at least one ethylenically unsaturated monomer or oligomer, which comprises (co)polymerizing the monomer or monomers/ oligomers in the presence of an initiator/regulator compound of formula (I), (II), (III) or (IV) under reaction conditions capable of effecting scission of the O—C bond to form two free radicals, the radical •C radical being capable of initiating polymerization.

The scission of the O—C bond can be effected by ultrasonic treatment, heating or exposure to electromagnetic radiation, ranging from γ to microwaves.

Preferably the scission of the O—C bond is effected by heating and takes place at a temperature of between 50° C. and 160° C.

The process may be carried out in the presence of an organic solvent or in the presence of water or in mixtures of organic solvents and water. Additional cosolvents or surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%. In many cases it is possible to polymerize without any solvent.

If organic solvents are used, suitable solvents or mixtures of solvents are typically pure alkanes (hexane, heptane, octane, isoctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

The aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically in the range of about 100:0 to about 10:90.

The process is particularly useful for the preparation of block copolymers.

Block copolymers are, for example, block copolymers of polystyrene and polyacrylate (e.g., poly(styrene-co-acrylate) or poly(styrene-co-acrylate-co-styrene). They are usefull as adhesives or as compatibilizers for polymer blends or as polymer toughening agents. Poly(methylmethacrylate-co-acrylate) diblock copolymers or poly(methacrylate-co-acrylate-co-methacrylate) triblock copolymers) are useful as dispersing agents for coating systeme, as coating additives (e.g. rheological agents, compatibilizers, reactive diluents) or as resin component in coatings(e.g. high solid paints) Block copolymers or styrene, (meth)acrylates and/or acrylonitrile are useful for plastics, elastomers and adhesives.

Furthermore, block copolymers of this invention, wherein the blocks alternate between polar monomers and non-polar monomers, are useful in many applications as amphiphilic surfactants or dispersants for preparing highly uniform polymer blends.

The (co)polymers of the present invention may have a number average molecular weight from 1 000 to 400 000 g/mol, preferably from 2 000 to 250 000 g/mol and, more preferably, from 2 000 to 200 000 g/mol. The number average molecular weight may be determined by size exclusive chromatography (SEC), gel permeation chromatography (GPC), matrix assisted laser desorption/ionization mass spectrometry (MALDI-MS) or, if the initiator carries a group which can be easily distinguished from the monomer (s), by NMR spectroscopy or other conventional methods.

The polymers or copolymers of the present invention have preferably a polydispersity of from 1.1 to 2, more preferably of from 1.2 to 1.8.

Thus, the present invention also encompasses in the synthesis novel block, multi-block, star, gradient, random, hyperbranched and dendritic copolymers, as well as graft copolymers.

The definitions are preferences for the different substituents given for the compounds, apply also for the composition and for the polymerization process. The polymers prepared by the present invention are useful for following applications: adhesives, detergents, dispersants, emulsifiers, surfactants, defoamers, adhesion promoters, corrosion inhibitors, viscosity improvers, lubricants, rheology modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerization is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be added to form a second block on the growing polymer chain in a second polymerization step. Therefore it is possible to carry out additional polymerizations with the same or different monomer(s) to prepare multi-block copolymers. Furthermore, since this is a radical polymerization, blocks can be prepared in essentially any order. One is not necessarily restricted to preparing block copolymers where the sequential polymerizing steps must flow from the least stabilized polymer intermediate to the most stabilized polymer intermediate, such as is the case in ionic polymerization. Thus it is possible to prepare a multi-block copolymer in which a polyacrylonitrile or a poly(meth)acrylate block is prepared first, then a styrene or butadiene block is attached thereto, and so on.

Furthermore, there is no linking group required for joining the different blocks of the present block copolymer. One can simply add successive monomers to form successive blocks.

A plurality of specifically designed polymers and copolymers are accessible by the present invention, such as star and graft (co)polymers as described, inter alia, by C. J. Hawker in Angew. Chemie. 1995, 107, pages 1623–1627, dendrimers as described by K. Matyaszewski et al. in Macromolecules 1996, Vol 29, No. 12, pages 4167–4171, graft (co) polymers as described by C. J. Hawker et al. in Macromol. Chem. Phys. 198, 155–166(1997), random copolymers as described by C. J. Hawker in Macromolecules 1996, 29, 2686–2688, or diblock and triblock copolymers as described by N. A. Listigovers in Macromolecules 1996, 29, 8992–8993.

Preferably a cooligomers or copolymer of star, comb or block structure is prepared.

Still further subjects of the invention are oligomer, cooligomer, polymer or copolymer prepared by said process and the use of a compound of formula (I), (II), (III), (IV), (V), (VI) or (VII) for the polymerization of ethylenically unsaturated monomers.

The following examples illustrate the invention.

A Preparation of Compounds

Example A1

(Compound 101)

A photoreactor is charged with 120 g (0.73 mol) of 4-ethylphenylacetate, 5 g (0.029 mol) of 4-hydroxy-2,2,6, 6-tetramethylpiperidin-1-oxyl and 16.9 g (0.115 mol) of t-butylperoxide. The red solution is flushed with nitrogen and is then irradiated at 20–25° C. using a mercury dipping lamp (Pyrex jacket). Subsequently, the reaction mixture is concentrated in a rotary evaporator and the residue is chromatographed over silica gel with hexane/ethyl acetate (6:4), affording 6.2 g (64% of theory) of compound 101 in the form of colourless crystals. m.p.: 65–67° C. Analysis calculated for $C_{19}H_{29}NO_4$: C 68.03%, H 8.71%, N 4.18%; found C 67.96%, H 8.85%, N 3.77%.

Example A2

(Compound 102)

5 ml of HCl (37%) are added, with stirring and at room temperature, to a solution consisting of 10 g (0.03 mol) of the compound 101 in 50 ml of methanol. After 30 minutes, the resulting residue is collected by filtration. The residue is slurried in water and the aqueous suspension is adjusted to pH 7–8 with solid sodium hydrogen carbonate and extracted with ether. The organic phase is then dried over $Na_2SO_4$ and concentrated in a rotary evaporator. This residue is recrystallised from toluene, affording 6.7 g (76% of theory) of compound 102 in the form of white crystals. m.p.: 97–99° C. Analysis calculated for $C_{17}H_{27}NO_3$: C 9.28%, N 4.77%; found C 70.36% H 9.33%, N 4.48%.

Example A3

(Compound 103)

2.3 ml (0.027 mol) of allyl bromide are added dropwise at 20° C. to a suspension consisting of 4.0 g (0.014 mol) of compound 102 and 3.7 g (0.027 mol) of $K_2CO_3$ in 40 ml of acetone. This mixture is then stirred for 6 hours at 60° C. The reaction mixture is filtered and the filtrate is then concentrated in a rotary evaporator. The residue is recrystallised from pentane, affording 2.6 g (58% of theory) of compound 103 in the form of white crystals, m.p.: 66.5–67.5° C. Analysis calculated for $C_{20}H_{31}NO_3$: C 72.03%, H 9.37%, N 4.20%; found C 71.46%, H 9.36%, N 4.27%.

Example A4

(Compound 104)

A solution consisting of 22.0 g (0.075 mol) of compound 102 and 3 g (0.075) of NaOH in 30 ml of acetone and 50 ml of water is added dropwise at 5–10° C. to a solution consisting of 4.2 g (0.023 mol) of cyanuric chloride in 50 ml of acetone. After stirring the mixture for 16 hours at room temperature, the precipitated residue is collected by filtration. The filter cake is washed thoroughly with water, methanol and ether, affording 19.1 g (88% of theory) in the form of a white solid. m.p.: 212–214° C. Analysis calculated for $C_{54}H_{78}N_6O_9$: C 67.89%, N 8.79%, found C 67.51%, H 8.24%, N 8.90%.

Example A5

(Compound 105)

In analogy to Example 3, 1 g (3.78 mmol) of α,α'-dibromo-p-xylene 2.45 g (8.35 mmol) of compound 102 and 1.15 g (8.32 mmol) of $K_2CO_3$ are reacted in 25 ml of acetone. The crude product is chromatographed over silica gel with methylene chloride/ethanol (10:2), giving 2.4 g (92% of theory) of compound 105 in the form of white crystals. m.p.: 139–141° C. Analysis calculated for $C_{42}H_{60}N_2O_6$: C 73.22%, H 8.78%; N 4.06%; found C 73.92%, H 8.57%, N 3.81%.

Example A6

(Compound 106)

In analogy to Example 3, 1 g (2.94 mmol) of 4,4'-bis (bromomethyl)biphenyl, 1.90 g (6.47 mmol) of compound 102 and 0.90 g (6.51 mmol) of $K_2CO_3$ are reacted in 20 ml of acetone. The crude product is chromatographed over silica gel with methylene chloride/ethanol (10:2), giving 2.15 g (95% of theory) of compound 106 in the form of white crystals. m.p.: 65–69° C. Analysis calculated for $C_{48}H_{64}N_2O_6$: C 75.35%, H 8.43%, N 3.66%; found C 74.51%, H 8.54%, N 3.40%.

Example A7

(Compound 107)

In analogy to Example 3, 5.0 g (0.011 mol) of 1,2,4,5-tetrakis(bromo-methyl)benzene, 15.0 g (0.051 mol) of compound 102 and 7.0 g (0.05 mol) of $K_2CO_3$ are reacted in 100 ml of acetone. The crude product is chromatographed over silica gel with methylene chloride/ethanol (10.3) and is then recrystallised from toluene, giving 9.1 g (63% of theory) of compound 107 in the form of white crystals. m.p.: 158–161° C. Analysis calculated for $C_{78}H_{114}N_4O_{12}$: C 72.08%, H 8.84%, N 4.31%; found C 71.53%, H 8.84%, N 3.99%.

Example A8

(Compound 108)

In analogy to Example 3, 5.0 g (7.86 mmol) of hexakis(bromomethyl)benzene, 15.6 g (53.1 mmol) of compound 102 and 7.4 g (53.5 mmol) of $K_2CO_3$ are reacted in 250 ml of acetone. The crude product is chromatographed over silica gel with methylene chloride/ethanol (10:3) and is then recrystallised from toluene, giving 13.3 g (89% of theory) of compound 108 in the form of white crystals. m.p.: 154–157° C. Analysis calculated for $C_{114}H_{168}N_6O_{18}$: C 71.66%, H 8.86%, N 4.39%; found C 71.64%, H 8.87%, N 4.06%.

Example A9

(Compound 109)

In analogy to Example 3, 1 ml (7.67 mmol) of ethyl 2-bromopropionate, 2.0 g (6.81 mmol) of compound 102 and 1.0 g (7.24 mmol) of $K_2CO_3$ are reacted in 10 ml of acetone. The crude product is chromatographed over silica gel with methylene chloride/ethanol (10:3), giving 2.25 g (84% of theory) of compound 109 in the form of a colourless oil. Analysis calculated for $C_{22}H_{35}NO_5$: C 67.15%, H 8.96%, N 3.56%; found C 67.05%, H 8.99%, N 3.52%.

Example A10

(Compound 110)

In analogy to Example 1, compound 110 is obtained in the form of white crystals from 1-t-butyl-3,3-diethyl-5,5-dimethyl-piperazin-2-on-4-oxyl and 4-ethylphenylacetate, m.p.: 92–96° C. Analysis calculated for $C_{24}H_{38}N_2O_4$: C 68.86%, H 15, N 6.69; found C 68.68%, H 9.10%, N 6.46%. 1-t-butyl-3,3-diethyl-5,5-dimethyl-piperazin-2-on-4-oxyl is prepared as described in EP Application No. 98811030.0.

Example A11

(Compound 111)

In analogy to Example 1, compound 111 is obtained in the form of white crystals from 1-t-butyl-3,3-diethyl-5,5-dimethyl-piperazin-2-on-4-oxyl and 4-ethylacetophenone, m.p.: 91–94° C. Analysis calculated for $C_{24}H_{36}N_2O_3$: C 71.60%, H 9.51%, N 6.96%; found C %71.03, H 9.49%, N 6.90%. 1-t-butyl-3,3-diethyl-5,5-dimethyl-piperazin-2-on-4-oxyl is prepared as described in EP Application No. 98811030.0

Example A12

(Compound 112)

16 g of potassium carbonate are added at a temperature from 11–20° C. to a solution consisting of 32.3 g (0.077 mol) of compound 110 in 250 ml of methanol. After stirring for 15 minutes, the reaction mixture is acidified with 2N-HCl and diluted with 500 ml of water. The precipitated residue is collected by suction filtration, washed with water and dried, giving 28.4 g (96%) of compound 112 in the form of beige microcrystalline powder, m.p. 145–147° C. $^1$H-NMR (300 MHz, CDCl$_3$), δ(ppm): (diastereomeric mixture): 7.17–6.76 m (4H), 4.65–4.54 m (1H), 3.14–2.93 m (2H), 2.13–0.55 m (28H).

Example A13

(Compound 113)

In analogy to Example 3, 2.64 g (0.01 mol) of α,α'-dibromo-p-xylene, 7.9 g (0.021 mol) of compound 112 and 2.8 g (0.02 mol) of $K_2CO_3$ are reacted in 30 ml of acetone. The crude product is chromatographed over silica gel with ethyl acetate/hexane (1:4), giving 4.4 g (51% of theory) of compound 113 in the form of a colourless resin. Analysis calculated for $C_{52}H_{78}N_4O_6$: C 73.03%, H 9.19%, N 6.55%; found C 73.17%, H 9.19%, N 6.55%.

Example A14

(Compound 114)

In analogy to Example 3, 2.25 g (0.005 mol) of 1,2,4,5-tetrakis(bromomethyl)benzene, 7.9 g (0.021 mol) of compound 112 and 2.8 g (0.02 mol) of $K_2CO_3$ are reacted in 40 ml of acetone. The crude product is chromatographed over silica gel with hexane/t-butylmethyl ether (3:1) and is then recrystallised from hexane, giving 5.1 g (62.5% of theory) of compound 114 in the form of white crystals. m.p.: 148–153° C. $^1$H-NMR (300 MHz, CDCl$_3$), δ(ppm): (diastereomeric mixture): 7.64 s (2H), 7.16–6.83 m (16H), 5.10 s (8H), 4.61–4.57 m (4H), 3.05–2.80 m (8H), 2.07–0.57 m (112H).

Example A15

Compound 115

In analogy to Example 3, 2.12 g (0.003 mol) of hexakis(bromomethyl)benzene, 7.9 g (0.021 mol) of compound 112 and 2.8 g (0.02 mol) of $K_2CO_3$ are reacted in 40 ml of acetone. The crude product is chromatographed over silica gel with hexane/ethyl acetate (4:1), giving 7.55 g (95% of theory) of compound 115 in the form of a colourless resin. $^1$H-NMR (300 MHz, CDCl$_3$), δ(ppm): (diastereomeric mixture): 7.24–6.84 m (24H), 5.20 bs (12H), 4.65–4.63 m (6H), 3.12–2.88 m (12H), 2.13–0.65 m (168H).

Example A16

Compound 116

3.1 ml (0.06 mol) of bromine are added dropwise, with cooling, to a solution consisting of 8 g (0.2 mol) of NaOH in 60 ml water, keeping the temperature below 10° C. A solution consisting of 8.05 g (0.02 mol) of compound 111 in 25 ml dioxane is then added dropwise and the mixture is stirred for 5 hours at a temperature from 10–20° C. Subsequently, 100 ml of water are added and the solution is extracted with 50 ml of methyl-t-butyl ether. The aqueous phase is acidified with HCl and extracted again with 2×50 ml of methyl-t-butyl ether. These extracts are then washed with water, dried over $MgSO_4$ and concentrated by evaporation. The residue is slurried in hexane, filtered and dried, giving 6.55 g (81%) of compound 116 in the form of a beige microcrystalline powder, m.p. 172–177° C. $^1$H-NMR (300 MHz, $CDCl_3$), δ(ppm): (diastereomeric mixture): 7.15 d (2H), 7.35 d (2H), 4.73–4.71 m (1H), 3.16–2.83 (2H), 2.11–0.60 m (28H).

Example A17

Compound 117

5.75 g (0.014 mol) of compound 116, 0.1 g of 4-dimethylaminopyridine, 1.31 g (0.0065 mol) of 1,12-dodecanediol and 2.95 g (0.014 mol) of dicyclohexylcarbodiimide are stirred in 25 ml of dichloromethane for 20 hours. After filtering the reaction mixture, the filtrate is chromatographed over silica gel with ethyl acetate/hexane (5:1), giving 4.95 g (78%) of compound 117 in the form of a colourless resin. Analysis calculated for $C_{58}H_{94}N_4O_8$: C 71.42%, H 9.71%, N 5.74%; found C 71.33%, H 9.66%, N 5.79%.

Example A18

Compound 118

In analogy to Example 117, 4.7 g (70%) of compound 118 are obtained in the form of a colourless resin from 7.1 g (0.00176 mol) of compound 116, 0.55 g (0.004 mol) of pentaerythritol, 0.1 g of 4-dimethylaminopyridine and 3.63 g (0.00176 mol) of dicyclohexylcarbodiimide in 25 ml of dichloromethane. $^1$H-NMR (300 MHz, $CDCl_3$), δ(ppm): (diastereomeric mixture): 7.91 d (8H), 7.28 d (8H), 4.83–4.76 m (4H), 4.73 bs (8H), 3.16–2.91 m (8H), 2.19–0.69 m (112H).

Example A19

Compound 119

In analogy to example A1 165 g (1 mol) of 4-ethylphenylacetate, 10 g (0.05 mol) of 4-hydroxy-2,6-diethyl-2,3,6-trimethylpiperidine-1-oxyl and 25 g (0.172 mol) of t-butylperoxide are reacted. The crude product is chromatographed over silica gel with ether/hexane (1:5), giving 8.5 g (45% of theory) of compound 119 in the form of a colorless resin.

Example A20

Compound 120

In analogy to example A2 34 g (0.09 mol) of of compound 119 are hydrolyzed with HCl. After work up 28.5 g of compound 120 are isolated as a yellow resin.

Example A21

Compound 121

In analogy to example A5, 3.1 g (0.012 mol) of α,α'-dibromo-p-xylene, 8.2 g (0.024 mol) of compound 120 and 1.15 g of $K_2CO_3$ are reacted in 50 ml of acetone. The crude product is chromatographed over silica gel with ether/hexane (1:5), giving 7.4 g (85% of theory) of compound 121 in the form of a white foam. Analysis calculated for $C_{48}H_{72}N_2O_5$: C 74.57%; H 9.38%; N 9.38%; N 3.62%; found C 74.73%; H 9.60%; N 3.62%.

Example A22

Compound 122

In analogy to example A7 3 g (0.0067 mol) of 1,2,3,4-tetrakis(bromo-methyl)benzene, 10.3 g (0.031 mol) of compound 120 and 4.2 g of $K_2CO_3$ are reacted in 50 ml of acetone. The crude product is chromatographed over silica gel with ether/hexane (2:5), giving 9.2 g (95% of theory) of compound 122 in the form of a colorless resin for which the analytical data correspond to the given structure.

Example A23

Compound 123

To 20 g (0.066 mol) of 1-{4-[1-(2,2,6,6-tetramethyl-piperidin-1-yloxy)-ethyl]-phenyl}-ethanone (prepared as described in WO 99/46261 example A4) in 40 ml ethanol 2 g (0.053 mol) of sodium borohydride were added. The reaction mixture was then stirred for 1 hour at 50° C. Subsequently, 50 ml of water are added and the solution is extracted with 2×50 ml of ethyl acetate. The organic phases are combined, dried over $Na_2SO_4$ and concentrated by evaporation. The crude product is chromatographed over silica gel with hexane/ethyl acetate (10:1), giving 16.2 g (81% of theory) of compound 123 in the form of a white crystalline powder, m.p.: 50–51° C.

Example A24

Compound 124

To a solution of 15 g (0.05 mol) of compound 123 and 5.9 g of triethylamine in 100 ml ether 4.9 g (0.053 mol) of acryloyl chloride are added drop wise under stirring at 0° C. The reaction mixture is then stirred for 4 hours at room temperature. Subsequently, the reaction mixture is washed twice with 50 ml water, dried over $Na_2SO_4$ and concentrated by evaporation. The crude product is chromatographed over silica gel with hexane/ethyl acetate (10:1), giving 6.7 g (38% of theory) of compound 124 in the form of a colourless liquid for which the analytical data correspond to the given structure. The compounds prepared are summarised in Table 1.

TABLE 1

| No. | Verbindung | No. | Verbindung |
|---|---|---|---|
| 101 | (structure) | 102 | (structure) |
| 103 | (structure) | 104 | (structure) |

TABLE 1-continued
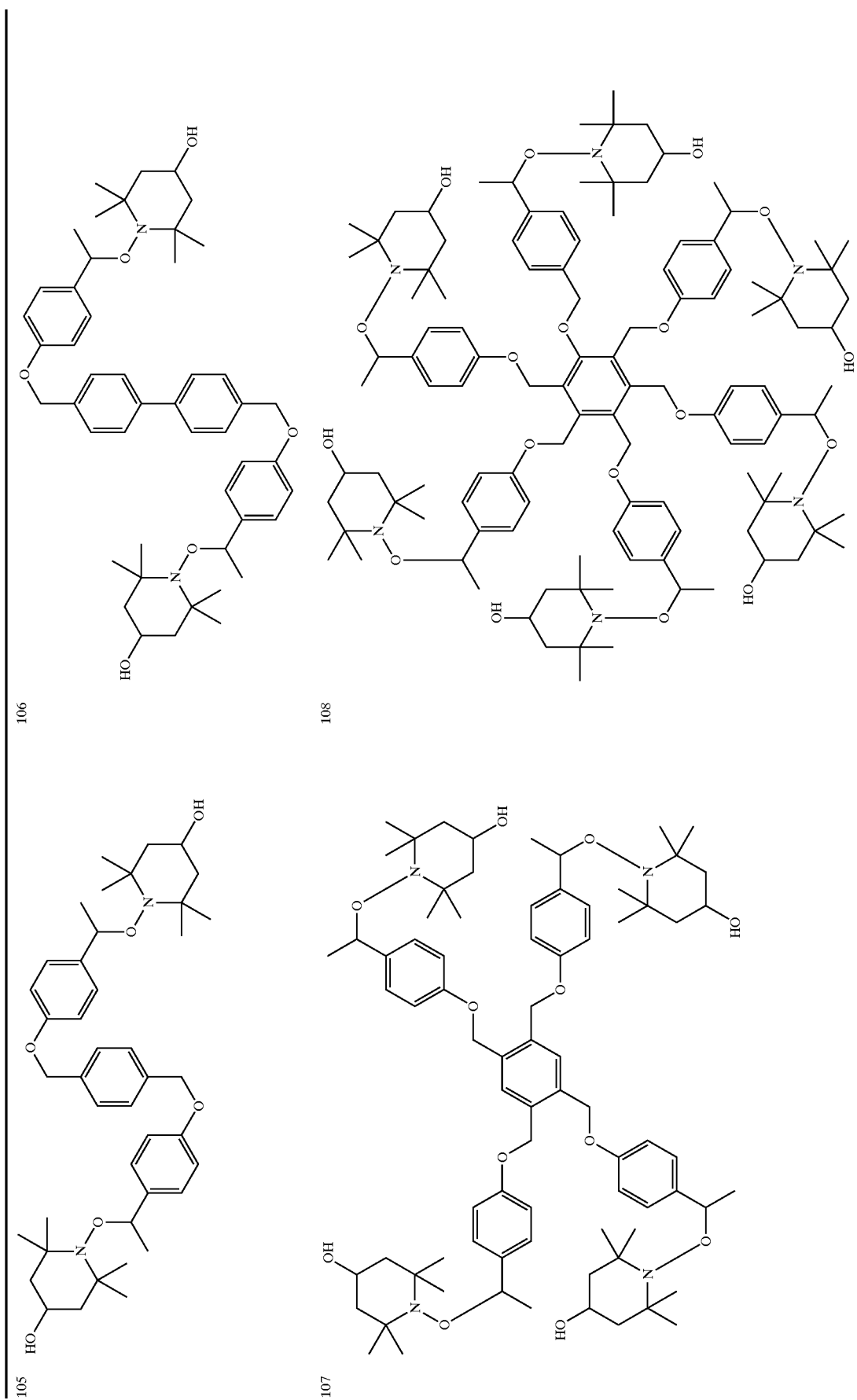
105
106
107
108

TABLE 1-continued
| 109 | 110 |
|---|---|
| 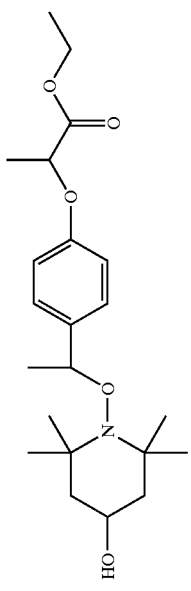 | 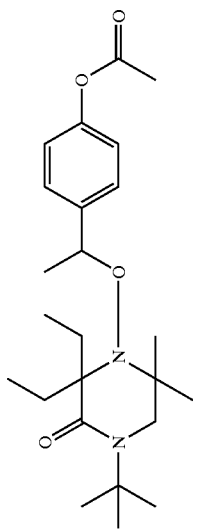 |
| 111 | 112 |
|---|---|
| 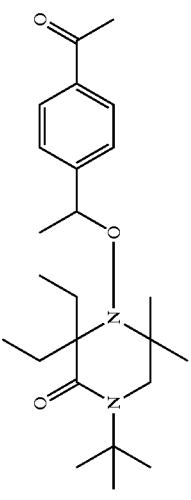 | 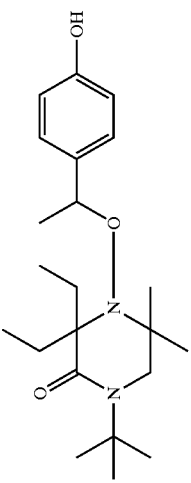 |

TABLE 1-continued
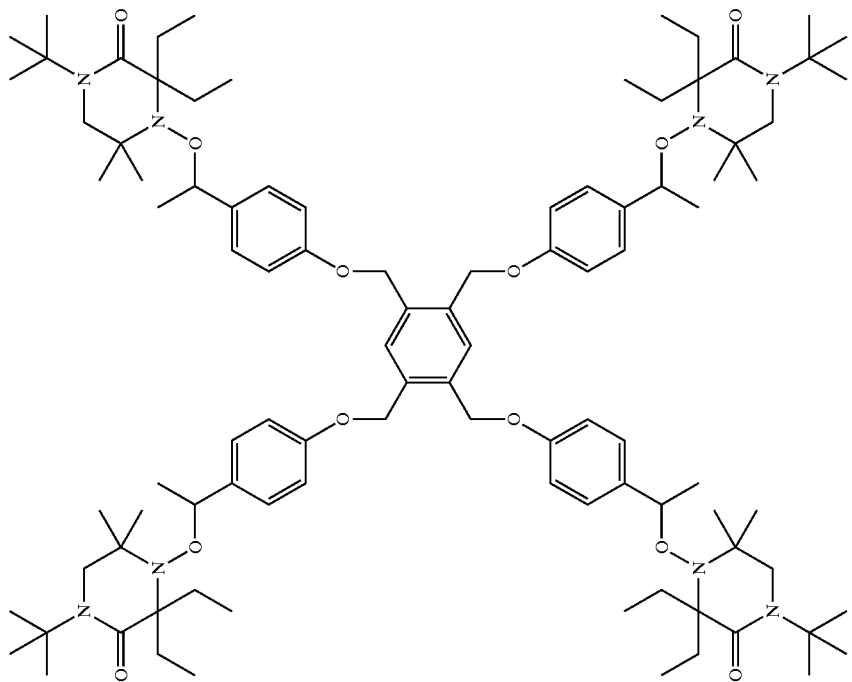
114
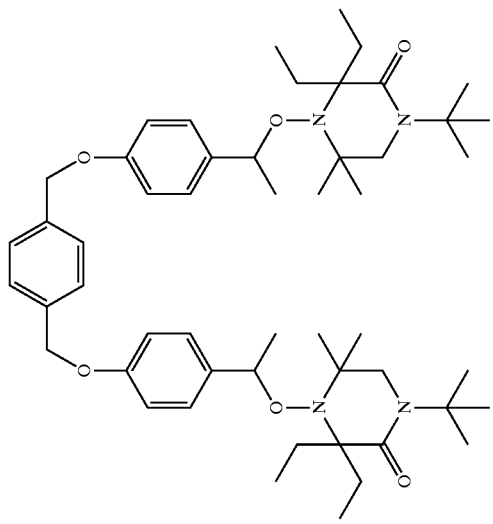
113

TABLE 1-continued
| No. | Verbindung |
|---|---|
| 115 | 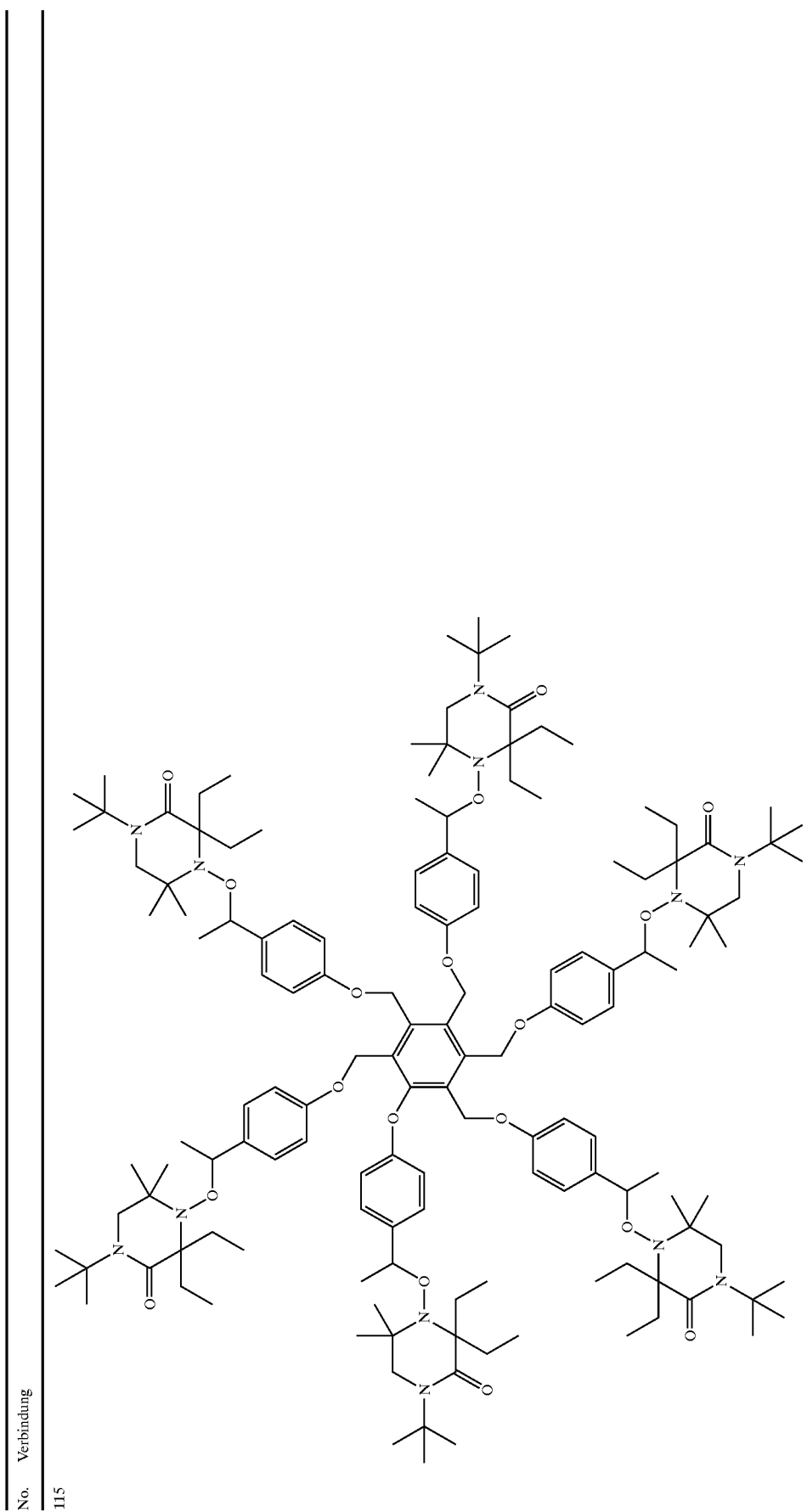 |

TABLE 1-continued

| No. | Verbindung |
|---|---|
| 116 | |
| 117 | |
| 118 | |

TABLE 1-continued
| No. | Verbindung | No. | Verbindung |
|---|---|---|---|
| 119 | 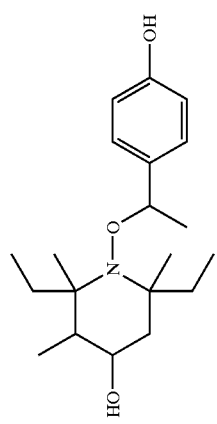 | 120 | 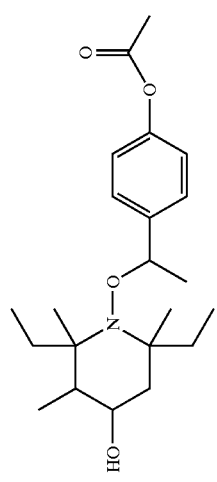 |
| 121 | 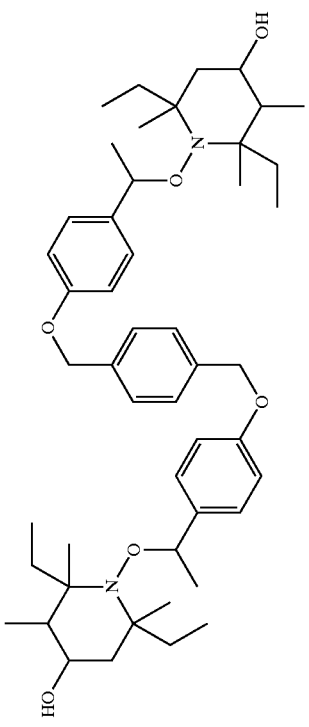 | 122 | 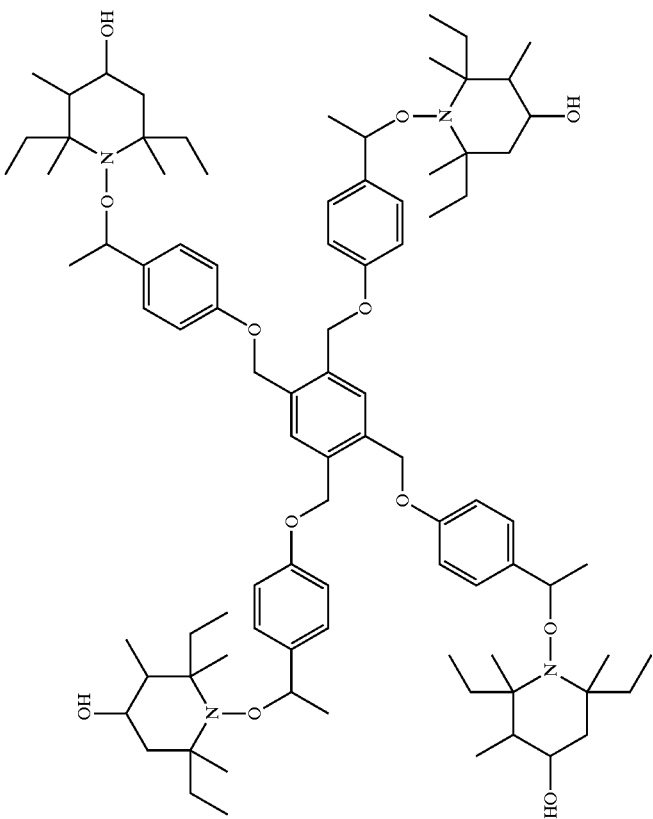 |

TABLE 1-continued

| No. | Verbindung |
|---|---|
| 123 | (structure) |
| 124 | (structure) |
| 125 | (structure) |
| 126 | (structure) |

The compounds 125–165 can be prepared in analogy to the examples give above.

Intermediate

| No. | Verbindung |
|---|---|
| 127 | (structure) |
| 128 | (structure) |
| 129 | (structure) |

TABLE 1-continued
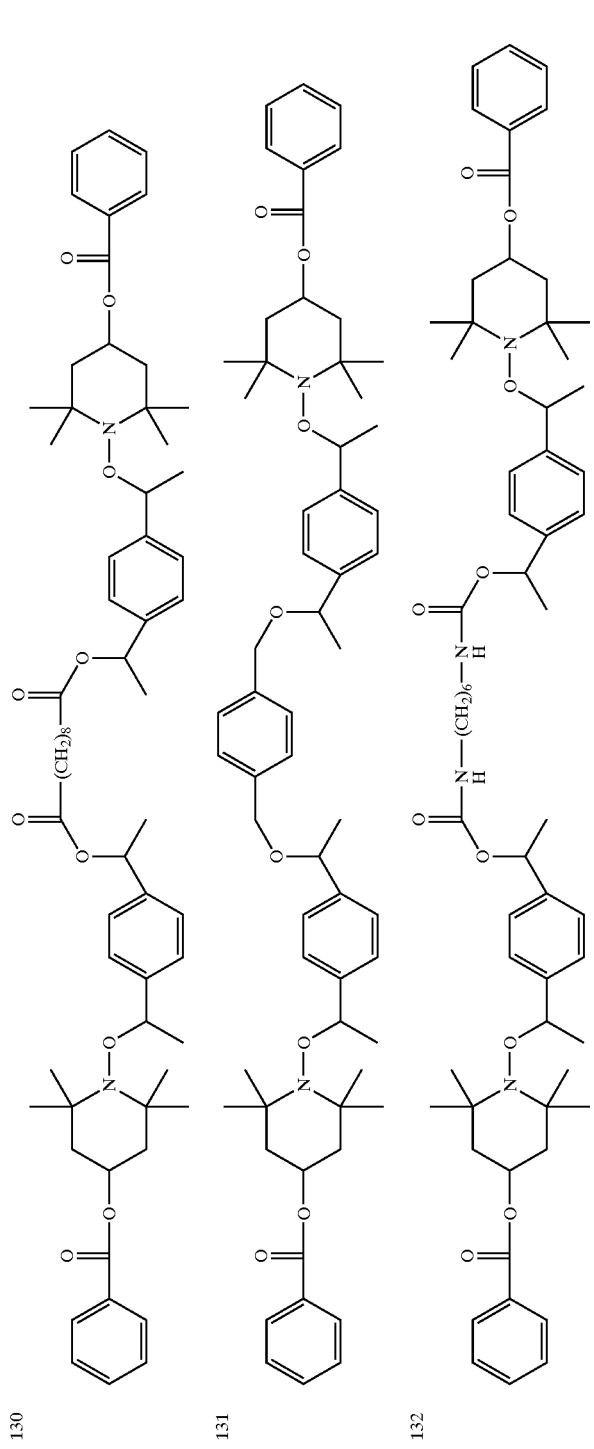
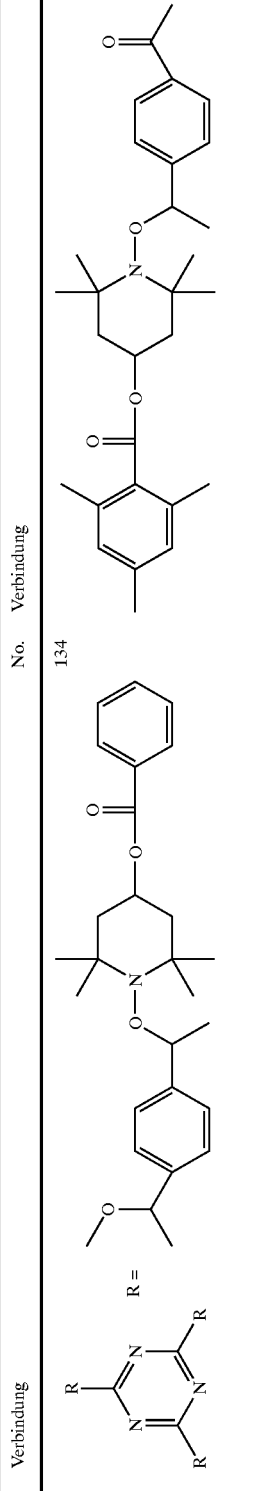
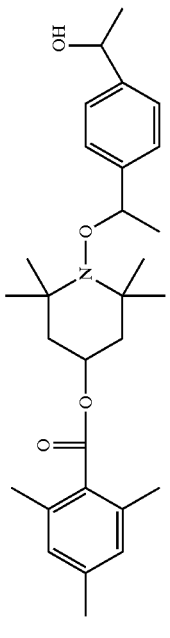

TABLE 1-continued
| No. | Verbindung |
|---|---|
| 136 |  |
| No. | Verbindung |
|---|---|
| 137 | Intermediate |
| 138 | Intermediate |
| 139 | |
| 140 | Intermediate |
| 141 | Intermediate |
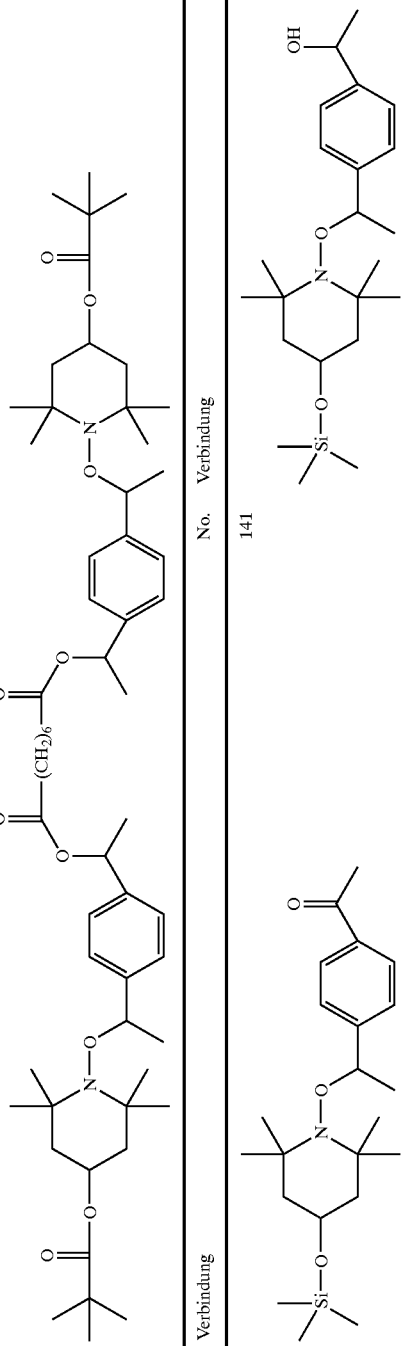

TABLE 1-continued
| No. | Verbindung |
|---|---|
| 142 |  |
| No. | Verbindung |
|---|---|
| 143 | Intermediate |
| No. | Verbindung |
|---|---|
| 144 | Intermediate |
| No. | Verbindung |
|---|---|
| 145 |  |
| No. | Verbindung |
|---|---|
| 146 | |
| No. | Verbindung |
|---|---|
| 147 | Intermediate |

TABLE 1-continued

| No. | Verbindung |
|---|---|
| 148 | |
| 149 | |
| 150 | Intermediate |
| 151 | |
| 152 | |
| 153 | Intermediate |

TABLE 1-continued

| No. | Verbindung |
|---|---|
| 154 | |
| No. | Verbindung |
| 155 | Intermediate |
| No. | Verbindung |
| 156 | |
| No. | Verbindung |
| 157 | |
| No. | Verbindung |
| 158 | Intermediate |
| No. | Verbindung |
| 159 | Intermediate |

TABLE 1-continued

| No. | Verbindung |
|---|---|
| 160 | |
| 161 | |
| 162 | |

| No. | Verbindung |
|---|---|
| 163 | |
| 164 | |
| 165 | |

TABLE 2

Polymerization examples
B) Polymerization of styrene with compounds 104, 105, 107 and 108
Reaction conditions: Schlenk flask, 50 ml styrene, Ar-purged
Regulator: amount of regulator corresponds to amount of styrene (50 ml = 0.436 mol).

| Compound | No. | Temp. (° C.) | Time (Hrs.) | amount of regulator | Conv. (%) | $M_n$ | $M_w$ | $M_w/M_n$ |
|---|---|---|---|---|---|---|---|---|
| 104 | B1 | 130 | 6 | 0.33 mol % | 51 | 13400 | 16900 | 1.26 |
| 104 | B2 | 130 | 6 | 0.033 mol % | 59 | 77500 | 140800 | 1.82 |
| 105 | B3 | 130 | 6 | 0.33 mol % | (42) | 11400 | 14900 | 1.30 |
| 105 | B4 | 130 | 6 | 0.033 mol % | (62) | 76700 | 124600 | 1.62 |
| 107 | B5 | 120 | 6 | 0.33 mol % | (25) | 6200 | 7800 | 1.26 |
| 107 | B6 | 130 | 6 | 0.33 mol % | (57) | 11600 | 17400 | 1.49 |
| 107 | B7 | 120 | 6 | 0.033 mol % | (39) | 5900 | 8900 | 1.51 |
| 107 | B8 | 130 | 6 | 0.033 mol % | (72) | 75000 | 148500 | 1.98 |
| 108 | B9 | 130 | 6 | 0.33 mol % | (34) | 7200 | 11500 | 1.61 |

C. Polymerization of Acrylates

Example C1

A 50 ml round-bottom three necked flask, equipped with thermometer, condenser and magnetic stirrer is charged with 0.441 g (1.17 mmol) of compound 112 and 10 g (78 mmol) of n-Butylacrylate and degassed. The clear solution is then heated to 145° C. under argon. The mixture is stirred for 5 hours at 145° C. and then cooled to 60° C. and the remaining monomer is evaporated under high vacuum. 4 g (40%) of the monomer are reacted and a colorless viscous liquid is obtained. GPC: Mn=4500, Mw=5600, Polydispersity index=1.25

Example C2

A 50 ml round-bottom three necked flask, equipped with thermometer, condenser and magnetic stirrer is charged with 1.601 g (1.872 mmol) of compound 113 and 8 g (62.4 mmol) of n-Butylacrylate and degassed. The clear solution is then heated to 145° C. under argon. The mixture is stirred for 3 hours at 145° C. and then cooled to 60° C. and the remaining monomer is evaporated under high vacuum. 5.68 g (71%) of the monomer are reacted and a clear yellow viscous liquid is obtained. GPC: Mn=4300, Mw=4900, Polydispersity index=1.15

Example C3

A 50 ml round-bottom three necked flask, equipped with thermometer, condenser and magnetic stirrer is charged with 1.528 g (0.936 mmol) of compound 114 and 8 g (62.4 mmol) of n-Butylacrylate and degassed. The clear solution is then heated to 145° C. under argon. The mixture is stirred for 3 hours at 145° C. and then cooled to 60° C. and the remaining monomer is evaporated under high vacuum. 5.2 g (65%) of the monomer are reacted and a clear yellow viscous liquid is obtained. GPC: Mn=8500, Mw=9700, Polydispersity index=1.15

Example C4

A 50 ml round-bottom three necked flask, equipped with thermometer, condenser and magnetic stirrer is charged with 2.255 g (0.936 mmol) of compound 115 and 8 g (62.4 mmol) of n-Butylacrylate and degassed. The clear solution is then heated to 145° C. under argon. The mixture is stirred for 3 hours at 145° C. and then cooled to 60° C. and the remaining monomer is evaporated under high vacuum. 4.8 g (60%) of the monomer are reacted and a yellow viscous liquid is obtained. GPC: Mn=7400, Mw=8100, Polydispersity index=1.1

Example C5

A 50 ml round-bottom three necked flask, equipped with thermometer, condenser and magnetic stirrer is charged with 0.473 g (1.17 mmol) of compound 116 and 10 g (78 mmol) of n-Butylacrylate and degassed. The clear solution is then heated to 145° C. under argon. The mixture is stirred for 5 hours at 145° C. and then cooled to 60° C. and the remaining monomer is evaporated under high vacuum. 8.6 g (86%) of the monomer are reacted and a colorless viscous liquid is obtained. GPC: Mn=8100, Mw=12000, Polydispersity index=1.5

Example C6

A 50 ml round-bottom three necked flask, equipped with thermometer, condenser and magnetic stirrer is charged with 1.826 g (1.872 mmol) of compound 117 and 8 g (62.4 mmol) of n-Butylacrylate and degassed. The clear solution is then heated to 145° C. under argon. The mixture is stirred for 3 hours at 145° C. and then cooled to 60° C. and the remaining monomer is evaporated under high vacuum. 5.2 g (65%) of the monomer are reacted and a clear yellow viscous liquid is obtained. GPC: Mn=4700, Mw=5500, Polydispersity index=1.2

Example C7

A 50 ml round-bottom three necked flask, equipped with thermometer, condenser and magnetic stirrer is charged with 1.575 g (0.936 mmol) of compound 118 and 8 g (62.4 mmol) of n-Butylacrylate and degassed. The clear solution is then heated to 145° C. under argon. The mixture is stirred for 3 hours at 145° C. and then cooled to 60° C. and the remaining monomer is evaporated under high vacuum. 5.2 g (65%) of the monomer are reacted and a clear yellow viscous liquid is obtained. GPC: Mn=8400, Mw=9600, Polydispersity index=1.15

Example C8

Compound 121

A 50 ml round-bottom three necked flask, equipped with thermometer, condenser and magnetic stirrer is charged with 1.446 g (1.87 mmol) of compound 121 and 8 g (62.4 mmol) of n-Butylacrylate and degassed. The clear solution is then heated to 145° C. under argon. The mixture is stirred for 3 hours at 145° C. and then cooled to 60° C. and the remaining monomer is evaporated under high vacuum. 6.8 g (85%) of the monomer are reacted and a colorless viscous liquid is obtained. GPC: Mn=4100, Mw=4900, Polydispersity index=1.2

Example C9

Compound 122

A 50 ml round-bottom three necked flask, equipped with thermometer, condenser and magnetic stirrer is charged with 1.365 g (0.93 mmol) of compound 122 and 8 g (62.4 mmol) of n-Butylacrylate and degassed. The clear solution is then heated to 145° C. under argon. The mixture is stirred for 3 hours at 145° C. and then cooled to 60° C. and the remaining monomer is evaporated under high vacuum. 7.5 g (94%) of the monomer are reacted and a colorless viscous liquid is obtained. GPC: Mn=9100, Mw=11300, Polydispersity index=1.25

What is claimed is:

1. A compound of formula (I), (II) or (III)

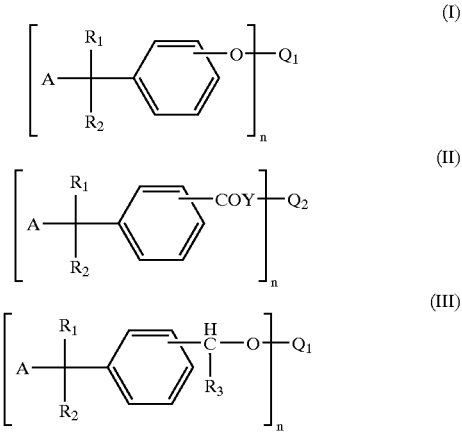

wherein $R_1$ and $R_2$ are independently of each other hydrogen, $C_1$–$C_{18}$alkyl, $C_3$–$C_{18}$alkenyl, $C_3$–$C_{18}$alkinyl or phenyl which are unsubstituted or substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino;

A is a group capable of forming a stable free nitroxyl radical A•, which is bound via its oxygen atom to the carbon atom;

Y is O, $NR_3$ or $CHR_3$—$X_a$, wherein $X_a$ is O, S or $NR_3$;

$R_3$ is hydrogen, $C_1$–$C_{18}$alkyl, $C_3$–$C_{18}$alkenyl, $C_3$–$C_{18}$alkinyl or phenyl which are unsubstituted or substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino;

$Q_1$ is an organic radical derived from an unsubstituted or substituted triazine, from a polycarboxylic acid or polycarboxylic acid derivative having 2–6 carboxylgroups, from a multifunctional alkylating agent having 2–6 functional groups or from a polyisocyanate having 2–6 isocyanate groups;

$Q_2$ is an organic radical derived from a mono or polyfunctional alcohol, mono or polyfunctional aminoalcohol, mono or polyfunctional amine mono or polyfunctional mercaptane, mono or polyfunctional phenol or mono or polyfunctional thiophenol; and n is a number from 2 to 10;

with the proviso, that in formula (I) if n is 2, $R_1$ is H and $R_2$ is —$CH_2$—O-tert-butyl, A is not 2,2,6,6-tetramethylpiperidine or 2,2,6,6-tetramethylpiperidine-4-carboxylic acid.

2. A compound of formula (I), (II) or (III) according to claim 1, wherein $R_1$ and $R_2$ are independently of each other hydrogen, $C_1$–$C_{12}$alkyl, $C_3$–$C_{12}$alkenyl or phenyl.

3. A compound of formula (II) according to claim 1, wherein Y is O or $NR_3$.

4. A compound of formula (II) according to claim 1, wherein $Q_2$ is an organic radical derived from a polyfunctional alcohol, a polyfunctional aminoalcohol or a polyfunctional amine.

5. A compound of formula (II) according to claim 4, wherein $Q_2$ is a radical derived from a polyalcohol having 2–6 hydroxy groups, a polyaminoalcohol having 2–6 amino and/or hydroxy groups, or a polyamine having 2–6 amine groups.

6. A compound of formula (I), (II) or (III) according to claim 1, wherein the radical A• derived from the group A is a stable open chain nitroxyl radical or a cyclic nitroxyl radical.

7. A compound of formula (I), (II) or (III) according to claim 1, wherein

A is a group of formula (X)

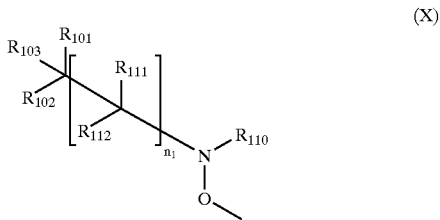

wherein $n_1$ is 0 or 1

$R_{101}$, $R_{102}$, $R_{103}$ are each independently of one another hydrogen, halogen, $NO_2$, cyano, —$CONR_{105}R_{106}$, —($R_{109}$)$COOR_{104}$, —C(O)—$R_{107}$, —$OR_{108}$, —$SR_{108}$, —$NHR_{108}$, —$N(R_{108})_2$, carbamoyl, di($C_1$–$C_{18}$alkyl)carbamoyl, —C(=$NR_{105}$)($NHR_{106}$);

unsubstituted $C_1$–$C_{18}$alkyl, $C_2$–$C_{18}$alkenyl, $C_2$–$C_{18}$alkynyl, $C_7$–$C_8$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl) amino; or phenyl, which is unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino;

or $R_{102}$ and $R_{103}$, together with the linking carbon atom, form a $C_3$–$C_{12}$cycloalkyl radical, a ($C_4$–$C_{12}$cycloalkanon)-yl radical or a $C_3$–$C_{12}$cycloalkyl radical containing at least one O atom and/or a $NR_{108}$ group; or if $n_1$ is 1

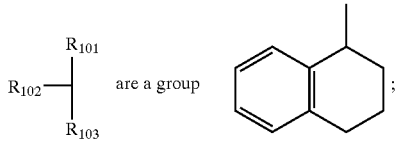 are a group $R_{104}$ is hydrogen, $C_1$–$C_{18}$alkyl, phenyl, an alkali metal cation or a tetraalkylammonium cation;

$R_{105}$ and $R_{106}$ are hydrogen, $C_1$–$C_{18}$alkyl which is substituted by at least one hydroxy group or, taken together, form a $C_2$–$C_{12}$alkylene bridge or a $C_2$–$C_{12}$-alkylene bridge interrupted by at least one O or/and $NR_{108}$ atom;

$R_{107}$ is hydrogen, $C_1$–$C_{18}$alkyl or phenyl;

$R_{108}$ is hydrogen, $C_1$–$C_{18}$alkyl or $C_2$–$C_{18}$alkyl which is substituted by at least one hydroxy group;

$R_{109}$ is $C_1$–$C_{12}$alkylen or a direct bond;

$R_{110}$ is $C_4$–$C_{18}$alkyl bound via a tertiary C-atom to the nitrogen atom, $C_9$–$C_{11}$phenylalkyl, $C_3$–$C_{12}$cycloalkyl or $C_3$–$C_{12}$cycloalkyl containing at least one nitrogen or oxygen atom; or $C_4$–$C_{18}$alkyl bound via a tertiary C-atom to the nitrogen atom, $C_9$–$C_{11}$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl) amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino;

if $n_1$ is 1

$R_{111}$ is $C_1$–$C_{18}$alkyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl) amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino or di($C_1$–$C_4$alkyl)amino; or a polycyclic cycloaliphatic ring system or a polycyclic cycloaliphatic ring system with at least one di- or trivalent nitrogen atom; or $R_{110}$ and $R_{111}$ together form a $C_2$–$C_{12}$alkylene bridge, a $C_3$–$C_{12}$alkylen-on bridge or a $C_2$–$C_{12}$alkylene bridge which is interrupted by at least one O or N atom, which bridges are unsubstituted or substituted with $C_1$–$C_{18}$alkyl, hydroxy($C_1$–$C_4$)alkyl, phenyl, $C_7$–$C_9$phenylalkyl, $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl)amino, $R_{112}$ is hydrogen, —($R_{109}$)$COOR_{104}$, cyano, —$OR_{108}$, —$SR_{108}$, —$NHR_{108}$, —$N(R_{108})_2$, —NH—C(O)—$R_{108}$, unsubstituted $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom; or $C_1$–$C_{18}$alkyl, $C_2$–$C_{18}$alkenyl, $C_2$–$C_{18}$alkynyl, $C_7$–$C_9$phenylalkyl, $C_3$–$C_{12}$cycloalkyl or $C_3$–$C_{12}$cycloalkyl containing at least one nitrogen or oxygen atom, which are substituted by $NO_2$, halogen, amino, hydroxy, cyano, carboxy, $C_1$–$C_4$alkoxy, $C_1$–$C_4$alkylthio, $C_1$–$C_4$alkylamino or di($C_1$–$C_4$alkyl) amino; or phenyl, naphthyl, which are unsubstituted or substituted by $C_1$–$C_4$alkyl, $C_1$–$C_4$alkoxy, $C_1$–$C_4$alkylthio, halogen, cyano, hydroxy, carboxy, $C_1$–$C_4$alkylamino, di($C_1$–$C_4$alkyl)amino; or $R_{111}$ and $R_{112}$ together with the linking carbon atom form a $C_3$–$C_{12}$cycloalkyl radical;

or A is a group of formula XXa, XXb or XXc

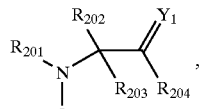 (XXa)

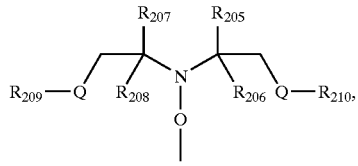 (XXb)

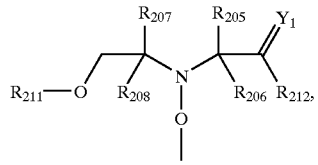 (XXc)

wherein $Y_1$ is O or $CH_2$;

Q is O or $NR_{220}$, wherein $R_{220}$ is hydrogen or $C_1$–$C_{18}$alkyl;

$R_{201}$ is tertiary $C_4$–$C_{18}$alkyl or phenyl, which are unsubstituted or substituted by halogen, OH, $COOR_{221}$ or C(O)—$R_{222}$ wherein $R_{221}$ is hydrogen, a alkali metal atom or $C_1$–$C_{18}$alkyl and $R_{222}$ is $C_1$–$C_{18}$alkyl; or $R_{201}$ is $C_5$–$C_{12}$cycloalkyl, $C_5$–$C_{12}$cycloalkyl which is interrupted by at least one O or N atom, a polycyclic alkyl radical or a polycyclic alkyl radical which is interrupted by at least one O or N atom;

$R_{202}$ and $R_{203}$ are independently $C_1$–$C_{18}$alkyl, benzyl, $C_5$–$C_{12}$cycloalkyl or phenyl, which are unsubstituted or substituted by halogen, OH, $COOR_{221}$ or C(O)—$R_{222}$ or together with the carbon atom form a $C_5$–$C_{12}$cycloalkyl ring;

if $Y_1$ is O, $R_{204}$ and $R_{212}$ are OH, O(alkali-metal) $C_1$–$C_{18}$alkoxy, benzyloxy, $NR_{223}R_{224}$, wherein $R_{223}$ and $R_{224}$ are independently from each other hydrogen, $C_1$–$C_{18}$alkyl or phenyl, which are unsubstituted or substituted by halogen, OH, $COOR_{221}$ or C(O)—$R_{222}$;

is $Y_1$ is $CH_2$, $R_{204}$ is OH, $C_1$–$C_{18}$alkoxy, benzyloxy, O—C(O)—($C_1$–$C_{18}$)alkyl or $NR_{223}R_{224}$;

$R_{212}$ are a group $C(O)R_{225}$, wherein $R_{225}$ is OH, $C_1$–$C_{18}$alkoxy, benzyloxy, $NR_{223}R_{224}$, wherein $R_{223}$ and $R_{224}$ are independently from each other hydrogen, $C_1$–$C_{18}$alkyl or phenyl, which are unsubstituted or substituted by halogen, OH, COOR$_{221}$ or C(O)—R$_{222}$;

$R_{205}$, $R_{206}$, $R_{207}$ and $R_{208}$ are independently of each other $C_1$–$C_{18}$alkyl, $C_5$–$C_{12}$cycloalkyl or phenyl; or $R_{205}$ and $R_{208}$ and/or $R_{207}$ and $R_{208}$ together with the carbon atom form a $C_5$–$C_{12}$cycloalkyl ring;

$R_{209}$ and $R_{210}$ are independently of each other hydrogen, formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, COOR$_{221}$ or C(O)—R$_{222}$;

$R_{211}$, is formyl, $C_2$–$C_{18}$alkylcarbonyl, benzoyl, $C_1$–$C_{18}$alkyl, $C_5$–$C_{12}$cycloalkyl, $C_5$–$C_{12}$cycloalkyl which is interrupted by at least one O or N atom, benzyl or phenyl which are unsubstituted or substituted by halogen, OH, COOR$_{221}$ or C(O)—R$_{222}$, or A is a group containing a structural element of formula (XXX)

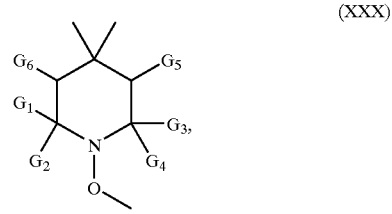

wherein $G_1$, $G_2$, $G_3$, $G_4$ are independently $C_1$–$C_6$alkyl or $G_1$ and $G_2$ or $G_3$ and $G_4$, or $G_1$ and $G_2$ and $G_3$ and $G_4$ together form a $C_5$–$C_{12}$cycloalkyl group;

$G_5$, $G_6$ independently are H, $C_1$–$C_{18}$alkyl, phenyl, naphthyl or a group COOC$_1$–$C_{18}$alkyl;

or A is a group of formula (XLa) or (XLb)

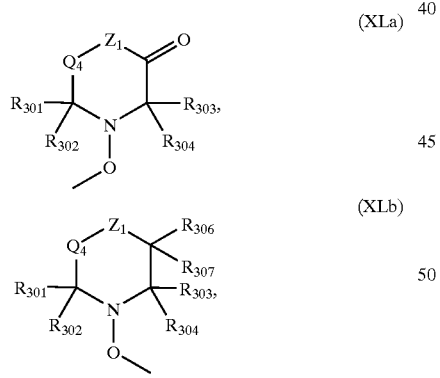

wherein $R_{301}$, $R_{302}$, $R_{303}$ and $R_{304}$ independently of each other are $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by OH, halogen or a group —O—C(O)—R$_{305}$, $C_2$–$C_{18}$alkyl which is interrupted by at least one O atom and/or NR$_{305}$ group, $C_3$–$C_{12}$cycloalkyl or $C_6$–$C_{10}$aryl or $R_{301}$ and $R_{302}$ and/or $R_{303}$ and $R_{304}$ together with the linking carbon atom form a $C_3$–$C_{12}$cycloalkyl radical;

$R_{305}$, $R_{306}$ and $R_{307}$ independently are hydrogen, $C_1$–$C_{18}$alkyl or $C_6$–$C_{10}$aryl;

$Z_1$ is O or NR$_{308}$;

$R_{308}$ is hydrogen, OH, $C_1$–$C_{18}$alkyl, $C_3$–$C_{18}$alkenyl, $C_3$–$C_{18}$alkinyl, $C_1$–$C_{18}$alkyl, $C_3$–$C_{18}$alkenyl, $C_3$–$C_{18}$alkinyl which are substituted by one or more OH, halogen or a group —O—C(O)—R$_{305}$, $C_2$–$C_{18}$alkyl which is interrupted by at least one O atom and/or NR$_{305}$ group, $C_3$–$C_{12}$cycloalkyl or $C_8$–$C_{10}$aryl, $C_7$–$C_9$phenylalkyl, $C_5$–$C_{10}$heteroaryl, —C(O)—$C_1$–$C_{18}$alkyl, —O—$C_1$–$C_{18}$alkyl or —COOC$_1$–$C_{18}$alkyl;

$Q_4$ is a direct bond or a divalent radical CR$_{309}$R$_{310}$, CR$_{309}$R$_{310}$—CR$_{311}$R$_{312}$, CR$_{309}$R$_{310}$CR$_{311}$R$_{312}$CR$_{313}$R$_{314}$, C(O) or CR$_{309}$R$_{310}$C(O), wherein R$_{309}$, R$_{310}$, R$_{311}$, R$_{312}$, R$_{313}$ and R$_{314}$ are independently hydrogen, phenyl or $C_1$–$C_{18}$alkyl.

8. A compound of formula (I) or (II) according to claim 7, wherein A is a group of formula (X)

$n_1$ is 1

$R_{101}$ is cyano;

$R_{101}$ and $R_{103}$ are each independently of one another unsubstituted $C_1$–$C_{12}$alkyl or phenyl; or $R_{102}$ and $R_{103}$, together with the linking carbon atom, form a $C_5$–$C_7$ cycloalkyl radical;

$R_{110}$ is $C_4$–$C_{12}$alkyl bound via a tertiary C-atom to the nitrogen atom, $C_9$–$C_{11}$phenylalkyl or phenyl;

$R_{11}$ is $C_1$–$C_{18}$alkyl, $C_7$–$C_9$phenylalkyl or $C_3$–$C_{12}$cycloalkyl; or $R_{110}$ and $R_{111}$ together form a $C_2$–$C_6$alkylene bridge which is unsubstituted or substituted with $C_1$–$C_4$alkyl; and $R_{112}$ is $C_1$–$C_4$alkyl;

or wherein A is a group of formula (XXa)

$R_{201}$ is tertiary $C_4$–$C_8$alkyl;

$R_{202}$ and $R_{203}$ are methyl, ethyl or together with the carbon atom form a $C_5$–$C_6$cycloalkyl ring;

$R_{204}$ is $C_1$–$C_{18}$alkoxy, benzyloxy or NR$_{223}$R$_{224}$, wherein $R_{223}$ and $R_{224}$ are independently of each other hydrogen or $C_1$–$C_8$alkyl;

or wherein A is a group of formula (XXb), wherein Q is O;

$R_{205}$, $R_{206}$, $R_{207}$ and $R_{208}$ are independently of each other methyl or ethyl; or $R_{205}$ and $R_{206}$ and/or $R_{207}$ and $R_{208}$ together with the carbon atom form a $C_5$–$C_6$cycloalkyl ring;

$R_{209}$ and $R_{210}$ are independently of each other formyl, $C_2$–$C_8$alkylcarbonyl, benzoyl, $C_1$–$C_8$alkyl, benzyl or phenyl;

or wherein A is a group of formula (XXc), wherein $Y_1$ is O;

$R_{205}$, $R_{206}$, $R_{207}$ and $R_{208}$ are independently of each other methyl or ethyl; or $R_{205}$ and $R_{206}$ and/or $R_{207}$ and $R_{208}$ together with the carbon atom form a $C_5$–$C_6$cycloalkyl ring;

$R_{211}$ is formyl, $C_2$–$C_{18}$alkylcarbonyl, benzoyl, $C_1$–$C_{18}$alkyl, benzyl or phenyl and $R_{212}$ is OH, $C_1$–$C_{18}$alkoxy, benzyloxy, NR$_{223}$R$_{224}$, wherein $R_{223}$ and $R_{224}$ are independently of each other hydrogen or $C_1$–$C_{18}$alkyl, or wherein A is a group of formula (XXXA), (XXXB) or (XXXO)

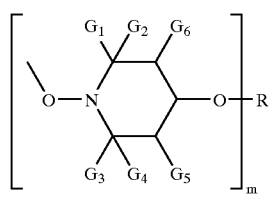

(XXXA)

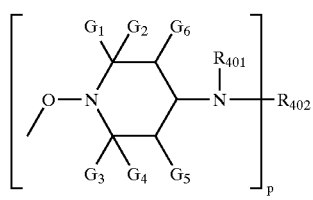

(XXXB)

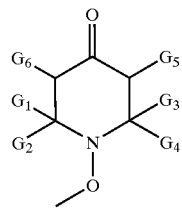

(XXXO)

wherein

G₁, G₂, G₃ and G₄ are independently alkyl of 1 to 4 carbon atoms, or G₁ and G₂ together and G₃ and G₄ together, or G₁ and G₂ together or G₃ and G₄ together are pentamethylene;

G₅ and G₆ are independently hydrogen or $C_1$–$C_4$ alkyl;

m is a number from 1–4;

p is a number from 1–3;

R, if m is 1, is hydrogen, $C_1$–$C_{18}$alkyl which is uninterrupted or $C_2$–$C_{18}$alkyl which is interrupted by one or more oxygen atoms, cyanoethyl, benzoyl, glycidyl, a monovalent radical of an aliphatic carboxylic acid having 2 to 18 carbon atoms, of a cycloaliphatic carboxylic acid having 7 to 15 carbon atoms, or an α,β-unsaturated carboxylic acid having 3 to 5 carbon atoms or of an aromatic carboxylic acid having 7 to 15 carbon atoms, where each carboxylic acid can be substituted in the aliphatic, cycloaliphatic or aromatic moiety by 1 to 3 —COOZ₁₂ groups, in which Z₁₂ is H, $C_1$–$C_{20}$alkyl, $C_3$–$C_{12}$alkenyl, $C_5$–$C_7$cycloalkyl, phenyl or benzyl; or R is a monovalent radical of a carbamic acid or phosphorus-containing acid or a monovalent silyl radical;

R, if m is 2, is $C_2$–$C_{12}$alkylene, $C_4$–$C_{12}$alkenylene, xylylene, a divalent radical of an aliphatic dicarboxylic acid having 2 to 36 carbon atoms, or a cycloaliphatic or aromatic dicarboxylic acid having 8–14 carbon atoms or of an aliphatic, cycloaliphatic or aromatic dicarbamic acid having 8–14 carbon atoms, where each dicarboxylic acid may be substituted in the aliphatic, cycloaliphatic or aromatic moiety by one or two —COOZ₁₂ groups; or R is a divalent radical of a phosphorus-containing acid or a divalent silyl radical;

R, is m is 3, is a trivalent radical of an aliphatic, cycloaliphatic or aromatic tricarboxylic acid, which may be substituted in the aliphatic, cycloaliphatic or aromatic moiety by —COOZ₁₂, of an aromatic tricarbamic acid or of a phosphorus-containing acid, or is a trivalent silyl radical, R, if m is 4, is a tetravalent radical of an aliphatic, cycloaliphatic or aromatic tetracarboxylic acid;

p is 1, 2 or 3,

R₄₀₁ is $C_1$–$C_{12}$alkyl, $C_5$–$C_7$cycloalkyl, $C_7$–$C_8$aralkyl, $C_2$–$C_{18}$alkanoyl, $C_3$–$C_5$alkenoyl or benzoyl;

when p is 1,

R₄₀₂ is $C_1$–$C_{18}$alkyl, $C_5$–$C_7$cycloalkyl, $C_2$–$C_8$alkenyl unsubstituted or substituted by a cyano, carbonyl or carbamide group, or is glycidyl, a group of the formula —CH₂CH(OH)—Z₄ or of the formula —CO—Z₄— or —CONH—Z₄ wherein Z₄ is hydrogen, methyl or phenyl; or when p is 2, R₄₀₂ is $C_2$–$C_{12}$alkylene, $C_6$–$C_{12}$-arylene, xylylene, a —CH₂CH(OH)CH₂—O—B—O—CH₂CH(OH)CH₂— group, wherein B is $C_2$–$C_{10}$alkylene, $C_8$–$C_{15}$arylene or $C_8$–$C_{12}$cycloalkylene; or, provided that R₄₀₁ is not alkanoyl, alkenoyl or benzoyl; or R₄₀₂ is a divalent acyl radical of an aliphatic, cycloaliphatic or aromatic dicarboxylic acid or dicarbamic acid, or is the group —CO—; or R₄₀₁ and R₄₀₂ together when p is 1 can be the cyclic acyl radical of an aliphatic or aromatic 1,2- or 1,3-dicarboxylic acid; or R₄₀₂ is a group

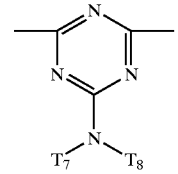

where T₇ and T₈ are independently hydrogen, alkyl of 1 to 18 carbon atoms, or T₇ and T₈ together are alkylene of 4 to 6 carbon atoms or 3-oxapentamethylene;

when p is 3,

R₄₀₂ is 2,4,6-triazinyl;

or wherein in formula (XLa) or (XLb)

R₃₀₁, R₃₀₂, R₃₀₃ and R₃₀₄ independently of each other are $C_1$–$C_4$alkyl, which is unsubstituted or substituted by OH, or a group —O—C(O)—R₃₀₅, or R₃₀₁ and R₃₀₂ and/or R₃₀₃ and R₃₀₄ together with the linking carbon atom form a $C_5$–$C_6$cycloalkyl radical;

R₃₀₅ is hydrogen or $C_1$–$C_4$alkyl,

R₃₀₆ and R₃₀₇ independently are hydrogen, methyl or ethyl;

Z₁ is O or NR₃₀₈;

Q₄ is a direct bond or a divalent radical CH₂, CH₂CH₂, CH₂—CH₂—CH₂, C(O), CH₂C(O) or CH₂—CH—CH₃;

R₃₀₈ is hydrogen, $C_1$–$C_4$alkyl, $C_1$–$C_4$alkyl which is substituted by OH, or benzyl.

9. A compound according to claim 8, wherein in formula (XXXA), (XXXB) or (XXXO) G₁ and G₃ are methyl and G₂ and G₄ are ethyl or propyl, or G₁ and G₂ are methyl and G₃ and G₄ are ethyl or propyl.

10. A compound according to claim 8, wherein in formula (XXXA) $G_1$ and $G_3$ are methyl and $G_2$ and $G_4$ are ethyl or propyl, or $G_1$ and $G_2$ are methyl and $G_3$ and $G_4$ are ethyl or propyl, one of $G_5$ and $G_6$ is hydrogen and the other is methyl or both are hydrogen, m is 1 and R is $C_1$–$C_{18}$alkyl or the monovalent radical of a $C_2$–$C_{18}$carboxylic acid.

11. A compound according to claim 7 wherein in formula (XLa) and (XLb) at least two of $R_{301}$, $R_{302}$, $R_{303}$ and $R_{304}$ are ethyl, propyl or butyl and the remaining are methyl.

12. A polymerizable composition, comprising
   a) at least one ethylenically unsaturated monomer or oligomer, and
   b) a compound of formula (I), (II) or (III) according to claim 1.

13. A polymerizable composition according to claim 12, wherein the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (meth)acrylonitriles, (alkyl)acrylamides, vinyl halides and vinylidene halides.

14. A process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of an initiator/regulator compound of formula (I), (II) or (III) according to claim 1 under reaction conditions capable of effecting scission of the O—C bond to form two free radicals, the •C radical being capable of initiating polymerization.

15. A process according to claim 14, wherein the scission of the O—C bond is effected by ultrasonic treatment, heating or exposure to electromagnetic radiation, ranging from γ to microwaves.

16. A process according to claim 14, wherein the scission of the O—C bond is effected by heating and takes place at a temperature of between 50° C. and 160° C.

17. A process according to claim 14, wherein a cooligomer or copolymer of star, comb or block structure is prepared.

18. A process according to claim 14, wherein the compound of formula (I), (II) or (III) is present in an amount of from 0.01 to 30 mol % based on the monomer or monomer mixture.

19. A oligomer, cooligomer, polymer or copolymer prepared by a process according to claim 14.

* * * * *

UNITED STATES PATENT AND TRADEMARK OFFICE
CERTIFICATE OF CORRECTION

PATENT NO. : 6,875,831 B1
DATED : April 5, 2005
INVENTOR(S) : Andreas Kramer et al.

It is certified that error appears in the above-identified patent and that said Letters Patent is hereby corrected as shown below:

<u>Title page,</u>
Item [86], should read -- PCT No.: PCT/EP00/05899
§ 371 ©(1),
(2), (4) Date: Dec. 20, 2001 --.

Signed and Sealed this

Twenty-eighth Day of June, 2005

JON W. DUDAS
*Director of the United States Patent and Trademark Office*